(12) United States Patent
Ahmad

(10) Patent No.: US 8,088,333 B2
(45) Date of Patent: Jan. 3, 2012

(54) THERMOELECTRIC SENSOR FOR ANALYTES IN A GAS

(75) Inventor: Lubna M. Ahmad, Chandler, AZ (US)

(73) Assignee: Invoy Technology, LLC, Chandler, AZ (US)

( * ) Notice: Subject to any disclaimer, the term of this patent is extended or adjusted under 35 U.S.C. 154(b) by 237 days.

(21) Appl. No.: 11/273,625

(22) Filed: Nov. 14, 2005

(65) Prior Publication Data

US 2006/0133960 A1    Jun. 22, 2006

Related U.S. Application Data

(63) Continuation-in-part of application No. 10/554,801, filed as application No. PCT/US2004/013364 on Apr. 28, 2004, now abandoned.

(60) Provisional application No. 60/465,949, filed on Apr. 28, 2003.

(51) Int. Cl.
G01N 31/22 (2006.01)
G01N 31/00 (2006.01)

(52) U.S. Cl. .............................. 422/88; 422/83; 422/50

(58) Field of Classification Search .................. 422/88, 422/85, 50; 128/844; 204/403.01, 415; 435/14; 374/10
See application file for complete search history.

(56) References Cited

U.S. PATENT DOCUMENTS

| | | |
|---|---|---|
| 1,997,659 A | 7/1929 | Styer |
| 3,552,207 A | 1/1971 | Monk et al. |
| 3,578,405 A | 5/1971 | Woodle |
| 3,904,371 A | 9/1975 | Neti et al. |
| 3,998,591 A | 12/1976 | Eckfeldt |
| 4,070,157 A | 1/1978 | Iles |
| 4,115,229 A | 9/1978 | Capone |
| 4,169,126 A | 9/1979 | Iles |
| 4,323,536 A | 4/1982 | Columbus |
| 4,337,654 A | 7/1982 | Austin et al. |
| 4,339,318 A | 7/1982 | Tanaka |
| 4,391,777 A | 7/1983 | Hutson |
| 4,414,839 A | 11/1983 | Dilley et al. |
| 4,430,192 A | 2/1984 | Maeda |
| 4,931,404 A | 6/1990 | Kundu |
| 4,935,345 A | 6/1990 | Guilbeau et al. |
| 4,962,025 A | 10/1990 | Moldowan |

(Continued)

FOREIGN PATENT DOCUMENTS

WO    03008942 A    1/2003

(Continued)

OTHER PUBLICATIONS

Ahmad L. "Towards Noninvasive Metabolic Monitoring: The Technical Feasibility of a Thermoelectric Acetone Sensor." Presentation on Dec. 2, 2005 at Arizona State University, USA.

(Continued)

Primary Examiner — Christine T Mui
(74) Attorney, Agent, or Firm — Roberts Mlotkowski Safran & Cole, P.C.

(57) ABSTRACT

An apparatus for sensing at least one analyte in a gas. The apparatus includes a thermoelectric sensor having a layer of at least one analyte interactant that increases or decreases in temperature and at least one thermopile having a first contact pad and a second contact pad, wherein the analyte contacts the interactant and produces or consumes heat, which is transmitted to the thermopile, produces a voltage difference and measures the analyte.

29 Claims, 11 Drawing Sheets

U.S. PATENT DOCUMENTS

| | | | |
|---|---|---|---|
| 4,970,172 | A | 11/1990 | Kundu |
| 5,018,395 | A | 5/1991 | Hickox |
| 5,071,769 | A | 12/1991 | Kundu |
| 5,087,312 | A | 2/1992 | Gerber |
| 5,108,576 | A | 4/1992 | Malmros |
| 5,113,874 | A * | 5/1992 | Maronian .................. 128/844 |
| 5,174,959 | A | 12/1992 | Kundu |
| 5,352,352 | A * | 10/1994 | Tsukada et al. ............. 204/415 |
| 5,356,217 | A | 10/1994 | Sheffield |
| 5,505,073 | A | 4/1996 | Gerblinger |
| 5,571,395 | A | 11/1996 | Park et al. |
| 5,656,142 | A | 8/1997 | Park |
| 5,962,335 | A | 10/1999 | Katzman |
| 6,015,533 | A | 1/2000 | Young |
| 6,067,989 | A | 5/2000 | Katzman |
| 6,186,958 | B1 | 2/2001 | Katzman et al. |
| 6,190,858 | B1 | 2/2001 | Persaud et al. |
| 6,221,026 | B1 | 4/2001 | Phillips |
| 6,234,006 | B1 | 5/2001 | Sunshine |
| 6,238,085 | B1 | 5/2001 | Higashi et al. |
| 6,289,286 | B1 * | 9/2001 | Andersson et al. ............. 702/19 |
| 6,417,424 | B1 | 7/2002 | Bewick-Sonntag et al. |
| 6,436,346 | B1 * | 8/2002 | Doktycz et al. ................ 422/51 |
| 6,491,643 | B2 | 12/2002 | Katzman et al. |
| 6,555,821 | B1 | 4/2003 | Himberg et al. |
| 6,572,543 | B1 | 6/2003 | Christopherson et al. |
| 6,582,376 | B2 | 6/2003 | Baghdassarian |
| 6,599,253 | B1 | 7/2003 | Baum et al. |
| 6,607,387 | B2 | 8/2003 | Mault |
| 6,609,068 | B2 | 8/2003 | Cranley et al. |
| 6,613,205 | B1 * | 9/2003 | Steiner et al. ............ 204/403.01 |
| 6,629,934 | B2 | 10/2003 | Mault et al. |
| 6,631,333 | B1 | 10/2003 | Lewis et al. |
| 6,658,915 | B2 | 12/2003 | Sunshine et al. |
| 6,709,405 | B2 | 3/2004 | Jonson |
| 6,787,776 | B2 | 9/2004 | Webber et al. |
| 6,790,178 | B1 | 9/2004 | Mault et al. |
| 6,846,654 | B1 | 1/2005 | Blackburn |
| 7,374,719 | B2 | 1/2005 | Anaokar et al. |
| 7,022,288 | B1 | 4/2006 | Boss |
| 7,141,210 | B2 | 11/2006 | Bell |
| 7,220,387 | B2 | 5/2007 | Flaherty et al. |
| 7,329,389 | B2 | 2/2008 | Horovitz |
| 7,338,637 | B2 | 3/2008 | Pease |
| 7,364,551 | B2 | 4/2008 | Allen |
| 2003/0056570 | A1 | 3/2003 | Shin |
| 2003/0186453 | A1 | 10/2003 | Bell |
| 2004/0018114 | A1 | 1/2004 | Wang et al. |
| 2004/0236244 | A1 | 11/2004 | Allen et al. |
| 2005/0076943 | A1 | 4/2005 | Cooper et al. |
| 2005/0084921 | A1 | 4/2005 | Cranley et al. |

FOREIGN PATENT DOCUMENTS

| | | |
|---|---|---|
| WO | 03/039367 A1 | 5/2003 |
| WO | 03/039483 A2 | 5/2003 |

OTHER PUBLICATIONS

Ahmad L, Guilbeau EJ. "Design of a Breath Ketone Sensor for Obesity Management." Poster Presentation, Fall Meeting of the Biomedical Engineering Society, Oct. 15, 2004, USA.

Ahmad L. "Soft Lithography as a Technique for Thermopile Development." Poster presentation at undergraduate bioengineering dept at Arizona State University on Apr. 26, 2002, USA.

Barnett D, Tassopoulos CN, Fraser TR. Breath Acetone And Blood Sugar Measurements In Diabetes. Clinical Science 1969; 37 (2): 570.

Bunka DH, Stockley PG. Aptamers come of age—at last. Nature Reviews 2006; 4: 588-596.

Byrne HA, Tieszen KL, Hollis S, Dornan TL, New JP. Evaluation Of An Electrochemical Sensor For Measuring Blood Ketones. Diabetes Care 2000. 23 (4): 500-503.

Dexter Research Center. Jul. 20, 2007. Dexter Research Corporation. Aug. 13, 2007 <http://www.dexterresearch.com>.

Dillner U, Kessler E, Poser S, et al. Thermal Simulation Of A Micromachined Thermopile-Based Thin-Film Gas Flow Sensor. Microelectronics Journal 1998; 29 (4-5): 291-297.

Dotan N, Alstock RT, et al. Anti-glycan antibodies as biomarkers for diagnosis and prognosis. Lupus 2006; 15: 442-450.

Dube DH, Bertozzi CR. Glycans in cancer and inflammation: potential for therapeutics and diagnostics. Nature Reviews 2005; 4: 477.

Gabius HJ, Andre S, et al. The sugar code: functional lectinomics. Biochimica et Biophysica Acta 2002; 1572: 165.

Giovannetti G et al. Study for a portable IR sensor to detect the blood temperature during coronary bypass implantation. Review of Scientific Instruments 2005; 76: 0843021-5.

Girard N. "Student develops non-invasive diabetes breath test." Arizona State University's State Press Apr. 9, 2003.

Godts P, et al. Peltier Effect For Measurement Of Fluid Thermal Property—Application For Designing New Thermal Sensors. Sensors And Materials 1996; 8 (5): 293-301.

Hashimoto S, Asao T, et al. a1-Acid Glycoprotein fucosylation as a marker of carcinoma progression and prognosis. Cancer 2004; 101(12): 2825-2836.

Hayden GF. Olfactory Diagnosis In Medicine. Postgraduate Medicine 1980; 67 (4): 110.

Jones AW. Breath Acetone Concentrations In Fasting Male-Volunteers—Further-Studies And Effect Of Alcohol Administration. Journal Of Analytical Toxicology 1998; 12 (2): 75-79.

Jones AW. Breath-Acetone Concentrations In Fasting Healthy-Men—Response Of Infrared Breath-Alcohol Analyzers. Journal Of Analytical Toxicology 1987; 11 (2): 67-69.

Khan A et al. Evaluation of a bedside blood ketone sensor: the effects of acidosis, hyperglycaemia and acetoacetate of sensor performance. Diabetic Medicine 2004; 21: 782-785.

Kirby R, Cho EJ, et al. Aptamer-based sensor arrays for the detection and quantification of proteins. Analytical Chemistry 2004; 76: 4066-4075.

Kratz E, et al. Alterations of branching and differential expression of sialic acid on alpha-1-acid glycoprotein in human seminal plasma. Clinica Chimica Acta 2003; 331: 87-95.

Kundu SK, Bruzek JA, Nair R, Judilla AM. Breath Acetone Analyzer—Diagnostic-Tool To Monitor Dietary-Fat Loss. Clinical Chemistry 1993; 39(1): 87-92.

Kundu SK, Judilla AM. Novel Solid-Phase Assay Of Ketone-Bodies In Urine. Clinical Chemistry 1991; 37 (9): 1565-1569.

Kupari M, Lommi J, Ventila M, Karjalainen U. Breath Acetone In Congestive-Heart-Failure. American Journal Of Cardiology 1995; 76 (14): 1076.

Larson J. "Getting fat feedback." Arizona Republic Jul. 8, 2004.

Lerchner J, Caspary D, Wolf G. Calorimetric Detection Of Volatile Organic Compounds. Sensors And Actuators B-Chemical 2000; 70 (1-3): 57-66.

Likhodii SS, Musa K, Cunnane SC. Breath Acetone As A Measure Of Systemic Ketosis Assessed In A Rat Model Of The Ketogenic Diet. Clinical Chemistry 2002; 48 (1): 115-120.

Loken SC. Breath Acetone And Ketone Metabolism In Obese And Diabetic Mice. Diabetes 1976; 25: 374-374 Suppl. 1.

Mathonat C, et al. Measurements Of Excess-Enthalpies At High-Temperature And Pressure Using A New-Type Of Mixing Unit. Journal Of Solution Chemistry 1994; 23 (11): 1161-1182.

Muehlbauer MJ, Guilbeau EJ, Towe BC. Applications And Stability Of A Thermoelectric Enzyme Sensor. Sensors And Actuators B-Chemical 1990; 2 (3): 223-232.

Muehlbauer MJ, Guilbeau EJ, Towe BC. Model For A Thermoelectric Enzyme Glucose Sensor. Analytical Chemistry 1989; 61 (1): 77-83.

Muralt P. Ferroelectric thin films for micro-sensors and actuators: a review. Journal of Micromechanical Microengineering 2000; 10: 136-146.

Musa-Veloso K, et al. Breath Acetone Is A Reliable Indicator Of Ketosis In Adults Consuming Ketogenic Meals. American Journal Of Clinical Nutrition 2002; 76 (1): 65-70.

Neiman J, et al. Combined Effect Of A Small Dose Of Ethanol And 36-Hr Fasting On Blood-Glucose Response . . . Alcohol And Alcoholism 1987; 22 (3): 265-270.

Nelson N, et al. Exhaled Isoprene And Acetone In Newborn Infants And In Children With Diabetes Mellitus. Pediatric Research 1998; 44 (3): 363-367.

Rooth G. Clinical Value Of Ketone Body Determinations In Brittle Diabetes. Acta Medica Scandinavica 1972; 191 (6): 549.

Sayer N, et al. Structural characterization of a 2'F-RNA aptamer that binds a HIV-1 SU glycoprotein, gp120. Biochem and Biophys Research Communications 2002; 293: 924-931.

Schreiter M, Gabl R, et al. Functionalized Pyroelectric Sensors for Gas Detection. Sensors and Actuators B 2006; 19: 255.

Schwarz M, et al. Serum anti-Glc(a1,4)Glc(a) antibodies as a biomarker for relapsing-remitting multiple sclerosis. Journal of the Neurological Sciences 2006; 244: 59-68.

Shiyan SD, Bovin NV. Carbohydrate composition and immunomodulatory activity of different glycoforms of a1-acid glycoprotein. Glycoconjugate Journal 1997; 14: 631-638.

Tian J, et al. Probing the binding of scutellarin to human serum albumin by circular dichroism, fluorescence spectroscopy, FTIR . . . Biomacromolecules 2004; 5(5): 1956-1961.

Trotter MD, Sulway MJ, Trotter E. Rapid Determination Of Acetone In Breath And Plasma. Clinica Chimica Acta 1971; 35 (1): 137.

Tuerk C, Gold L. Systematic Evolution of Ligands by Exponential Enrichment: RNA Ligands to Bacteriophage T4 DNA Polymerase. Science 1990; 249: 505-510.

Xensor Integration. Jul. 24, 2007. Xensor Integration BV. Aug. 13, 2007 <http://xensor.nl>.

Khan Asa, Talbot JA, et al. Bedside Ketone Sensor Retains Accuracy Despite Changes in pH And The Presence Of Potential Interferents. Diabetes 2002; 51: 418 Suppl. 2.

Ahmad L, et al. "Renal Failure Detection System." Poster presentation in undergraduate course poster session at Arizona State University on Dec. 14, 2004, USA.

Ahmad L, et al. "Design and Development of a Noninvasive Ammonia Detection System." Poster in undergraduate course poster session at Arizona State University on Apr. 22, 2005, USA.

Massick, SM. Diode Laser-Based Ketosis Sensor. DOD SBIR Awards 2002.

Walsh, J. End of the Spectrum: A Breath of Fresh Air in Diabetes Detection. Spectroscopy 2004; 19: 50. Also, description from MSU Technology Transfer Office.

Bischoff R, et al. On-line detection of volatile compounds in human breath. 4th European Congres of Oto-Rhino-Laryngology, Head and Neck Surgery 2000; 1369-1375.

U.S. Appl. No. 11/781,784, filed Jan. 3, 2008, Allen.

U.S. Appl. No. 11/737,631, filed Nov. 15, 2007, Flaherty et al.,/Apieron, Inc.

U.S. Appl. No. 10/205,710, filed Jan. 29, 2004, Wang et al.

U.S. Appl. No. 11/437,275, filed Mar. 1, 2007, Gabriel et al.

Auget, C., Seguin, J. L., Martorell, F., Moll, F., Torra, V., & Lerchner, J. (2006). Identification of micro-scale calorimetric devices. Journal of Thermal Analysis and Calorimetry, 86(2), 521-529.

Baier, V., Fodisch, R., Ihring, A., Kessler, E., Lerchner, J., Wolf, G., et al. (2005). Highly sensitive thermopile heat power sensor for micro-fluid calorimetry of biochemical processes. Sensors and Actuators a-Physical, 123-124, 354-359.

Balko, B., Berger, R. L., & Friaut, W. (1969). Stopped-Flow Calorimetry for Biochemical Reactions. Analytical Chemistry, 41(11), 1506-&.

Bataillard, P., Steffgen, E., Haemmerli, S., Manz, A., & Widmer, H. M. (1993). An Integrated Silicon Thermopile as Biosensor for the Thermal Monitoring of Glucose, Urea and Penicillin. Biosensors & Bioelectronics, 8(2), 89-98.

Bayraktar, T., & Pidugu, S. B. (2006). Characterization of liquid flows in microfluidic systems. International Journal of Heat and Mass Transfer, 49(5-6), 815-824.

Bhagat, A. A. S., Peterson, E. T. K., & Papautsky, I. (2007). A passive planar micromixer with obstructions for mixing at low Reynolds numbers. Journal of Micromechanics and Microengineering, 17(5), 1017-1024.

Bishop, P. L., Gibbs, J. T., & Cunningham, B. E. (1997). Relationship between concentration and hydrodynamic boundary layers over biofilms. Environmental Technology, 18(4), 375-385.

Bruylants, G., Wouters, J., & Michaux, C. (2005). Differential scanning calorimetry in life science: Thermodynamics, stability, molecular recognition and application in drug design. Current Medicinal Chemistry, 12 (17), 2011-2020.

Caspary, D., Schropfer, M., Lerchner, J., & Wolf, G. (1999). A high resolution IC-calorimeter for the determination of heats of absorption onto thin coatings. Thermochimica Acta, 337(1-2), 19-26.

Casquillas, G. V., Bertholle, F., Le Berre, M., Meance, S., Malaquin, L., Greffet, J. J., et al. (2008). Thermo-resistance based micro-calorimeter for continuous chemical enthalpy measurements. Microelectronic Engineering, 85(5-6), 1367-1369.

Chung, C. K., & Shih, T. R. (2008). Effect of geometry on fluid mixing of the rhombic micromixtures. Microfluidics and Nanofluidics, 4(5), 419-425.

Esfandyarpour, H., Fabian, R., Pease, W., & Davis, R. W. (2008). Picocalorimetric method for DNA sequencing. Journal of Vacuum Science & Technology B, 26(2), 661-665.

Estandyarpour, H., Zheng, B., Fabian, R., Pease, W., & Davis, R. W. (2008). Structural optimization for heat detection of DNA thermosequencing platform using finite element analysis. Biomicrofluidics, 2(2), 11.

Friedrich, D., Please, C., & Melvin, T. (2008). Optimisation of analyte transport in integrated microfluidic affinity sensors for the quantification of low levels of analyte. Sensors and Actuators B-Chemical, 131(1), 323-332.

Gervais, T., & Jensen, K. F. (2006). Mass transport and surface reactions in microfluidic systems. Chemical Engineering Science, 61(4), 1102-1121.

Gigras, A., & Pushpavanam, S. (2008). Early induction of secondary vortices for micromixing enhancement. Microfluidics and Nanofluidics, 5(1), 89-99.

Hagleitner, C., Lange, D., Hierlemann, A., Brand, O., & Baltes, H. (2002). CMOS single-chip gas detection system comprising capacitive, calorimetric and mass-sensitive microsensors. Ieee Journal of Solid-State Circuits, 37(12), 1867-1878.

Hu, G. Q., Gao, Y. L., & Li, D. Q. (2007). Modeling micropatterned antigen-antibody binding kinetics in a microfluidic chip. Biosensors & Bioelectronics, 22(7), 1403-1409.

Jiang, F., Drese, K. S., Hardt, S., Kupper, M., & Schonfeld, F. (2004). Helical flows and chaotic mixing in curved micro channels. Aiche Journal, 50(9), 2297-2305.

Johannessen, E. A., Weaver, J. M. R., Bourova, L., Svoboda, P., Cobbold, P. H., & Cooper, J. M. (2002). Micromachined nanocalorimetric sensor for ultra-low-volume cell-based assays. Analytical Chemistry, 74(9), 2190-2197.

Jones, F., Bailey, R., Wilson, S., & Hiestand, J. (2007). The effects of engineering design on heterogeneous biocatalysis in microchannels. Applied Biochemistry and Biotechnology, 137, 859-873.

Kjeang, E., Sinton, D., & Harrington, D. A. (2006). Strategic enzyme patterning for microfluidic biofuel cells. Journal of Power Sources, 158(1), 1-12.

Kurzawski, P., Hagleitner, C., & Hierlemann, A. (2006). Detection and discrimination capabilities of a multitransducer single-chip gas sensor system. Analytical Chemistry, 78(19), 6910-6920.

Kwak, B. S., Kim, B. S., Cho, H. H., Park, J. S., & Jung, H. T. (2008). Dual thermopile integrated microfluidic calorimeter for biochemical thermodynamics. Microfluidics and Nanofluidics, 5(2), 255-262.

Lee, J., Lim, K. G., Palmore, G. T. R., & Tripathi, A. (2007). Optimization of microfluidic fuel cells using transport principles. Analytical Chemistry, 79(19), 7301-7307.

Lerchner, J., Maskow, T., & Wolf, G. (2008). Chip calorimetry and its use for biochemical and cell biological investigations. Chemical Engineering and Processing, 47(6), 991-999.

Lerchner, J., Wolf, A., Buchholz, F., Mertens, F., Neu, T. R., Harms, H., et al. (2008). Miniaturized calorimetry—A new method for real-time biofilm activity analysis. Journal of Microbiological Methods, 74(2-3), 74-81.

Lerchner, J., Kirchner, R., et al. (2006). Determination of molar heats of absorption of enantiomers into thin chiral coatings by combined IC-calorimetric and microgravimetric (QMB) measurements II. Thermodynamics of enantio selectivity in modified cyclodextrins. Thermochimica Acta, 445(2), 98-103.

Lerchner, J., Wolf, A., Huttl, R., & Wolf, G. (2004). Direct monitoring of biochemical processes using micro-structured heat power detectors. Chemical Engineering Journal, 101(1-3), 187-194.

Lerchner, J., Wolf, A., Wolf, G., Baier, V., Kessler, E., Nietzsche, M., et al. (2006). A new micro-fluid chip calorimeter for biochemical applications. Thermochimica Acta, 445(2), 144-150.

Lerchner, J., Wolf, A., Wolf, G., & Fernandez, I. (2006). Chip calorimeters for the investigation of liquid phase reactions: Design rules. Thermochimica Acta, 446(1-2), 168-175.

Lerchner, J., Wolf, G., Torralba, A., & Torra, V. (1997). Ambient perturbation reduction in microsized calorimetric systems. Thermochimica Acta, 302(1-2), 201-210.

Lerchner, J., Seidel, J., Wolf, G., & Weber, E. (1996). Calorimetric detection of organic vapours using inclusion reactions with organic coating materials. Sensors and Actuators B-Chemical, 32(1), 71-75.

Li, Y., Vancura, C., Barrettino, D., Graf, M., Hagleitner, C., Kummer, A., et al. (2007). Monolithic CMOS multi-transducer gas sensor microsystem for organic and inorganic analytes. Sensors and Actuators B-Chemical, 126 (2), 431-440.

Manglik, R. M., & Bergles, A. E. (2004). Enhanced heat and mass transfer in the new millennium: A review of the 2001 literature. Journal of Enhanced Heat Transfer, 11(2), 87-118.

Masud, M. M., Kuwahara, M., Ozaki, H., & Sawai, H. (2004). Sialyllactose-binding modified DNA aptamer bearing additional functionality by SELEX. Bioorganic & Medicinal Chemistry, 12(5), 1111-1120.

Minakov, A. A., & Schick, C. (2007). Ultrafast thermal processing and nanocalorimetry at heating and cooling rates up to 1 MK/s. Review of Scientific Instruments, 78(7).

Muehlbauer, M. J., Guilbeau, E. J., Towe, B. C., & Brandon, T. A. (1990). Thermoelectric Enzyme Sensor for Measuring Blood-Glucose. Biosensors & Bioelectronics, 5(1), 1-12.

Pennathur, S., Meinhart, C. D., & Soh, H. T. (2008). How to exploit the features of microfluidics technology. Lab on a Chip, 8(1), 20-22.

Perez-Herranz, V., Guinon, J. L., & Garcia-Anton, J. (2000). A new technique for the visualization of the concentration boundary layer in an electrodialysis cell. Journal of Applied Electrochemistry, 30(7), 809-816.

Rida, A., & Gijs, M. A. M. (2004). Manipulation of self-assembled structures of magnetic beads for microfluidic mixing and assaying. Analytical Chemistry, 76(21), 6239-6246.

Salemme, F. R. (2004). High-throughput biochemistry heats up. Nature Biotechnology, 22(9), 1100-1101.

Squires, I. M., Messinger, R. J., & Manalis, S. R. (2008). Making it stick: convection, reaction and diffusion in surface-based biosensors. Nature Biotechnology, 26(4), 417-426.

Torres, F. E., Kuhnt, P., De Bruyker, D., Bell, A. G., Wolkin, M. V., Peeters, E., et al. (2004). Enthalpy arrays. Proceedings of the National Academy of Sciences of the United States of America, 101(26), 9517-9522.

Towe, B. C., & Guilbeau, E. J. (1996). A vibrating probe thermal biochemical sensor. Biosensors & Bioelectronics, 11(3), 247-252.

van Herwaarden, A. W. (2005). Overview of calorimeter chips for various applications. Thermochimica Acta, 432 (2), 192-201.

Vandyke, M. (1994). 19th-Century Roots of the Boundary-Layer Idea. Siam Review, 36(3), 415-424.

Verhaegen, K., Baert, K., Simaels, J., & Van Driessche, W. (2000). A high-throughput silicon microphysiometer. Sensors and Actuators a-Physical, 82(1-3), 186-190.

Wang, H. Z., Iovenitti, P., Harvey, E., & Masood, S. (2002). Optimizing layout of obstacles for enhanced mixing m microchannels. Smart Materials & Structures, 11(5), 662-667.

Weber, P. C., & Salemme, F. R. (2003). Applications of calorimetric methods to drug discovery and the study of protein interactions. Current Opinion in Structural Biology, 13(1), 115-121.

Xu, J., Reiserer, R., Tellinghuisen, J., Wikswo, J. P., & Baudenbacher, F. J. (2008). A microfabricated nanocalorimeter: Design, characterization, and chemical calibration. Analytical Chemistry, 80(8), 2728-2733.

Yoon, S. I., Lim, M. H., Park, S. C., Shin, J. S., & Kim, Y. J. (2008). Neisseria meningitidis detection based on a microcalorimetric biosensor with a split-flow microchannel. Journal of Microelectromechanical Systems, 17(3), 590-598.

Yoon, S. K., Fichtl, G. W., & Kenis, P. J. A. (2006). Active control of the depletion boundary layers in microfluidic electrochemical reactors. Lab on a Chip, 6(12), 1516-1524.

Zhang, Y. Y., & Tadigadapa, S. (2004). Calorimetric biosensors with integrated microfluidic channels. Biosensors & Bioelectronics, 19(12), 1733-1743.

Zhou, R., Hierlemann, A., Weimar, U., & Gopel, W. (1996). Gravimetric, dielectric and calorimetric methods for the detection of organic solvent vapours using poly(ether urethane) coatings. Sensors and Actuators B-Chemical, 34(1-3), 356-360.

Lawrence, David J. et al., "Thermopile Sensors for the Detection of Airborne Pollutants", IEEE Sensors 2007 Conference, pp. 1237-1240.

Haug, M. et al., "Chemical Sensors Based Upon Polysiloxanes: comparison between optical, quartz microbalance, calorimetric, and capacitance sensors", Sensors and Actuators B, 11 (1993), pp. 383-391.

Schierbaum, K.D. et al., "Selective Detection of Organic Molecules With Polymers and Supramolecular Compounds: application of capacitance, quartz microbalance and calorimetric transducers", Sensors and Actuators A, 31 (1992), pp. 130-137.

Andersen, M. Y.; Pedersen, N. H.; Brabrand, H.; Hallager, L.; Jorgensen, S.B. "Regulation of a Continuous Yeast Bioreactor Near the Critical Dilution Rate Using a Productostat". Journal of Biotechnology 54. 1997. 1-14.

Anderson, J.C.; Lamm, W.J.E.; Hlastala, M.P. "Measuring Airway Exchange of Endogenous Acetone Using a Single-exhalation Breathing Maneuver". J Appl Physiol, 100. 2006. 880-889.

Barker, M.; Hengst, M.; Schmid, J.; Buers, H-J.; Mittermaier, B.; Klemp, D.; Koppmann, R "Volatile Organic Compounds in the Exhaled Breath of Young Patients with Cystic Fibrosis". Eur Respir J, 27. 2006. 929-936.

Barzana, E.; Klibanov, A.M.; Karel, M. "A Colorimetric Method for the Enzymatic Analysis of Gases: the Determination of Ethanol and Formaldehyde Vapors Using Solid Alcohol Oxidase". Analytical Biochemistry, 182. 1989. 109-115.

Bjarnason, B.; Johansson, P.; Johansson, G. "A Novel Thermal Biosensor: Evaluation for Determination of Urea in Serum". Analytica Chimica Acta, 372. 1998. 341-348.

Burritt, M.F. "Current Analytical Approaches to Measuring Blood Analytes". Clinical Chemistry, 36. 1990. 1562-1566.

Cooper, A.; Johnson, C.M. "Introduction to Microcalorimetry and Biomolecular Energetics". Methods in Molecular Biology, 22.1994. 109-124.

Crofford, O.B.; Mallard, R.E.; Winton, R.E.; Rogers, N. L.; Jackson, J.C.; Keller, U. "Acetone in Breath and Blood". Trans Am Clin Climatol Assoc, 88. 1977. 128-139.

Dubowski, K.M.; Essary, N.A. "Response of Breath-alcohol Analyzers to Acetone". Journal of Analytical Toxicology, 7. 1983. 231-234.

Dubowski, K.M.; Essary, N.A. "Response to Breath-alcohol Analyzers to Acetone: Further Studies". Journal of Analytical Toxicology, 8. 1984. 205-208.

Eklund, S.E.; Snider, R.M.; Wikswo, J.; Baudenbacher, F.; Prokop, A.; Cliffel, D.E. "Multianalyte Microphysiometry as a Tool in Metabolomics and Systems Biology". Journal of Electroanalytical Chemistry, 587. 2006. 333-339.

Fenske, J.D.; Paulson, S.E. "Human Breath Emissions of VOCs". Journal of Air & Waste Management Association, 49. 1999. 594-598.

Gage, J.C.; Lagesson, V.; Tunek, A. "A Method for the Determination of Low Concentrations of Organic Vapours in Air and Exhaled Breath". Annals of Occupational Hygiene, 20. 1977. 127-134.

Guilbeau, E.J.; Clark, L.C.; Pizziconi, V.B.; Schultz, J.S.; Towe, B.C. "Biosensors in Artificial Organs". ASAIO Trans, 33. 1987. 834-837.

Guilbeau, E.J.; Mayall, B.I. "Microthermocouple for Soft Tissue Temperature Determination". IEEE Transactions on Biomedical Engineering, 28. 1981. 301-305.

Guilbeau, E.J.; Towe, B.C.; Muehlbauer, M.J. "A Potentially Implantable Thermoelectric Sensor for Measurement of Glucose". ASAIO Trans, 33. 1987. 329-335.

Harper, M. "The Use of Thermal Desorption in Monitoring for the Chemical Weapons Demilitarization Program". J Environ Monit, 4. 2002. 688-694.

Harper, D.E.; Waldrop, R.D. "Infant Diabetic Ketoacidosis in the Emergency Department". Southern Medical Journal, 89. 1996. 729-731.

Hart, R.M.; Jones, J.D. "A New Micro Reaction Calorimeter". Journal of Thermal Analysis, 49. 1997. 1115-1119.

Hillaire, A.; Favre, E. "Isothermal and Nonisothermal Permeation of an Organic Vapor through a Dense Polymer Membrane". Ind. Eng. Chem. Res, 38. 1999. 211-217.

Huttl, R.; Bohmhammel, K; Pritzkat, K.; Wolf, G. "Problems Associated with Using Thermal Measurement Principles in Enzymatic Reactions". Thermochimica Acta, 229. 1993. 205-213.

Jensen, K.F. "Microreaction Engineering—Is Small Better?" Chemical Engineering Science, 56. 2001. 293-303.

Kohler, J.M.; Kessler, E.; Steinhage, G.; Grundig, B.; Cammann, K. "Thermoelectrical Micro-calorimetry and Microanalysis on Freestanding Membranes". Mikrochimica Acta, 120. 1995. 309-319.

Kohler, J.M.; Steinhage, G.; Krause, J.; Cammann, K. "Microanalytical Estimation of Cerium by a Miniaturized Thermoelectrical Sensor". Sensors and Actuators B. 23. 1995. 83-91.

Kohler, J.M.; Zieren, M. "Chip Reactor for Microfluid Calorimetry". Thermochimica Acta, 310. 1998. 25-35.

Kohler, J.M.; Zieren, M. "Micro Flow Calorimeter for Thermoelectrical Detection of Heat of Reaction in Small Volumes". Fresenius Journal of Analytical Chemistry, 358. 1997. 683-686.

Lerchner, J.; Wolf, A.; Wolf, G. "Recent Developments in Integrated Circuit Calorimetry". Journal of Thermal Analysis and Calorimetry, 57. 1999. 241-251.

Lestina, D.C.; Lund, A.K. "Laboratory Evaluation of Two Passive Alcohol Sensors". Journal of Studies on Alcohol, 53. 1992. 328-334.

Lucklum, R.; Henning, B.; Hauptmann, P. "Quartz Microbalance Sensors for Gas Detection". Sensors and Actuators A, 25-27. 1991. 705-710.

Makisimovich, N.; Vorotyntsev, V.; Nikitina, N.; Kaskevich, O.; Karabun, P.; Martynenko, F. "Adsorption Semiconductor Sensor for Diabetic Ketoacidosis Diagnosis". Sensors and Actuators B, 35-36. 1996. 419-421.

Mathis, T.R. "Development of a Thin Film Thermoelectric-immobilized Enzyme Glucose Sensor". Master of Science, Arizona State University. 1985. Abstract Only.

Matsumoto, K.; Matsubara, H.; Hamada, M.; Ukeda, H.; Osajima, Y. "Simultaneous Determination of Glucose, Ethanol and Lactate in Alcoholic Beverages and Serum by Amperometric Flow Injection Analysis with Immobilized Enzyme Reactors". Journal of Biotechnology, 14. 1990. 115-126.

McCall, J.K. "A Thin Film Thermal Enzyme Electrode for Detection of Glucose". Master of Science, Arizona State University. 1986. Abstract Only.

McGlashan, M.L.; Stoeckli, H.F. "A Flow Calorimeter for Enthalpies of Mixing the Enthalpy of Mixing of n-Hexane + Cyclohexane at 298.15 K". The Journal of Chemical Thermodynamics, 1. 1969. 589-594.

Miekisch, W.; Schubert, J.K.; Noeldge-Schomburg, G.F.E. "Diagnostic Potential of Breath Analysis—Focus on Volatile Organic Compounds" Clinica Chimica Acta, 347. 2004. 25-39.

Monk, P.; Wadso, I. "A Flow Micro Reaction Calorimeter". Acta Chemica Scandinavica, 22. 1968. 1842-1852.

Paulsson, N. J.P.; Winquist, F. "Analysis of Breath Alcohol with a Multisensor Array: Instrumental Setup, Characterization and Evaluation". Forensic Science International, 105. 1999. 95-114.

Pizziconi, V.B.; Page, D.L. "A Cell-based Immunobiosensor with Engineered Molecular Recognition—Part I: Design Feasibility". Biosensors & Bioelectronics, 12. 1997. 287-299.

Reichel, J.; Seyffarth, T.; Guth, U.; Mobius, H.H.; Gockeritz, D. "[Detection and Determination of Acetone Using Semiconductor Sensors]". Pharmazie, 44. 1989. 698-701.

Rhemrev-Boom, M.M.; Korf, J.; Venema, K.; Urban, G.; Vadgama, P. "A Versatile Biosensor Device for Continuous Biomedical Monitoring" Biosensors & Bioelectronics, 16. 2001. 839-847.

Schierbaum, K.D.; Weimar, U.; Gopel, W. "Multicomponent Gas Analysis: An Analytical Chemistry Approach Applied to Modified SnO2 Sensors". Sensors & Actuators B, 2. 1990. 71-78.

Schilz, J. "Thermoelectric Infrared Senors (Thermopiles) for Remote Temperature Measurements; Pyrometry" Thermophysica Minima. 2000. 1-12.

Schmidt, W.; Schieferdecker, J. "Understanding Thermopile Infrared Sensors". Perkin Elmer. 2003. 5 pgs.

Shah, M.R.; Noble, R.D.; Clough, D.E. "Measurement of Sorption and Diffusion in Nonporous Membranes by Transient Permeation Experiments". Journal of Membrane Science, 287. 2007. 111-118.

Towe, B.C. "Vibration of Polarographic Oxygen Electrodes by Piezoelectric Elements: a Method of Reducing Flow Artifacts". IEEE Transactions on Biomedical Engineering, 34. 1987. 657-663.

Towe, B.C.; Pizziconi, V.B. "A Microflow Amperometric Glucose Biosensor". Biosensors & Bioelectronics, 12. 1997. 893-899.

Urban, G.; Kamper, H.; Jachimowicz, A.; Kohl, F.; Kuttner, H.; Olcaytug, F.; Goiser, P.; Pittner, F.; Schalkhammer, T.; Mann-Buxbaum, E. "The Construction of Microcalorimetric Biosensors by Use of High Resolution Thin-film Thermistors". Biosensors & Bioelectronics, 6. 1991. 275-280.

Van Herwaarden, A.W.; Sarro, P.M.; Gardner, J.W.; Bataillard, P. "Liquid and Gas Micro-calorimeters for Bio(Chemical) Measurements". Sensors and Actuators A, 43. 1994. 24-30.

Wang, L.; Lin, Q. Q "Theory and Experiments of Mems Thermal Biosensors". IEEE Engineering in Medicine and Biology 27th Annual Conference. 2005. Shanghai, China. 1301-1304.

Wolf, A.; Weber, A.; Huttl, R.; Lerchner, J.; Wolf, G. "Sequential Flow Injection Analysis Based on Calorimetric Detection". Thermochimica Acta, 337. 27-38. 1999.

Xie, B.; Mecklenburg, M.; Danielsson, B.; Orman, O.; Norlin, P.; Winquist, F. "Development of an Integrated Thermal Biosensor for the Simultaneous Determination of Multiple Analytes". Analyst, 120. 1995. 155-160.

Xie, B.; Mecklenburg, M.; Danielsson, B.; Ohman, O.; Winquist, F. "Microbiosensor Based on an Integrated Thermopile". Analytica Chimica Acta, 299. 1994. 165-170.

Xie, B.; Ramanathan, K.; Danielsson, B. "Mini / Micro Thermal Biosensors and Other Related Devices for Biochemical / Clinical Analysis and Monitoring". Trends in Analytical Chemistry, 19. 2000. 340-349.

Xie, B.; Tang, X.; Wollenberger, U.; Johansson, G.; Gorton, L.; Scheller, F.; Danielsson, B. "Hybrid Biosensor for Simultaneous Electrochemical and Thermometric Direction". Analytical Letters, 30. 1997 2141-2158.

Yotter, R.A.; Lee, L.A.; Wilson, D.M. "Sensor Technologies for Monitoring Metabolic Activity in Single Cells—Part I: Optical Methods". IEEE Sensors, 4. 2004. 395-411.

Zhang, Y.; Tadigadapa, S. "Microthermopiles Integrated with Fluidic Channels as Calorimetric MEMS Biosensors". Transducers '03, The 12th International Conference on Solid State Sensors, Actuators and Microsystems. 2003. Boston, MA. 1176-1179.

Zieren, M.; Kohler, J.M. "A Micro-fluid Channel Calorimeter Using BiSB/Sb Thin Film Thermopiles". Transducers '97, 1997 International Conference on Solid-State Sensors and Actuators. 1997. Chicago, IL. 539-542.

Reisman, D.J. "Acetone". Environmental Health Criteria 207. Geneva: World Health Organization. 1998.

Bell C.M. "Attaining Specificity in the Measurement of Ethanol in Breath" (1990) Acta Med Leg Soc (Liege), 40, 107-111, Australia (Abstract Only).

Bengt Danielsson, "Calorimetric Biosensors", Journal of Biotechnology, 1990, pp. 187-200, vol. 15, Elsevier, Sweden.

Jennifer K. McCall "A Thin Film Thermal Enzyme Electrode for Detection of Glucose" (1986) Master of Science, Arizona State University.

Michael Joseph Muehlbauer "The Design and Characterization of an Implantable Thermoelectric Enzyme Glucose Sensor" (1988) Ph.D. Dissertation, Arizona State University, Tempe.

Michael Joseph Muehlbauer "The Design Fabrication and Characterization of a Thin Film Thermopile" (1985) Master of Science, Arizona State University, Tempe.

Timothy Robert Mathis "Development of a Thin Film Thermoelectric-immobilized Enzyme Glucose Sensor" (1985) Master of Science, Arizona State University.

Kumaran Ramanathan et al.,"Principles and Applications of Thermal Biosensors". Biosensors & Bioelectronics, 2001, pp. 417-423, vol. 16, Elsevier, Sweden.

* cited by examiner

THERMOELECTRIC SENSOR FOR ANALYTES IN A GAS

RELATED APPLICATIONS

This patent application is a continuation-in-part of application Ser. No. 10/554,801, filed on Oct. 28, 2005, directed to a Thermoelectric Biosensor for Analytes in a Gas, which claims priority to PCT/US2004/013364, filed on Apr. 28, 2004, which claims priority to application Ser. No. 60/465,949, filed on Apr. 28, 2003, the contents of each of which are hereby incorporated by reference in their entirety.

FIELD

The invention relates generally to an apparatus and method of detecting analytes in a gas and more specifically to a thermoelectric sensor for measuring analytes, for example, in expired air for monitoring biochemical processes such as in diabetes, epilepsy, or weight loss.

BACKGROUND

Ketone bodies provide a supplementary or substitute form of energy that can be used during various metabolic states including stress, starvation, caloric regulation, or pathology. Oftentimes in diabetics, for example, low insulin levels and elevated blood glucose levels result in high concentrations of ketones in the body. This could potentially cause diabetic ketoacidosis (DKA).

The epidemic of diabetes in the United States will contribute to staggering medical costs, which can be limited by close ketone monitoring and maintenance. Patients in DKA experience many symptoms such as nausea, fatigue, and rapid breathing. They also emit a fruity odor in their breath, which is distinct and attributable to acetone. Acetone is a volatile ketone body released into alveolar air.

Untreated, DKA can result in coma or even death. However, DKA is preventable if ketone levels are monitored and treatment is sought when ketone counts are high. The current methods of ketone measurement are blood and urine analysis. The current blood tests typically are accurate, but their invasive nature is undesirable and frequently causes patients to delay treatment. Blood tests also are expensive, as a number of products are needed, including a lancet for blood letting, test strips, a specialized device and batteries. Several studies show that urine analysis is not accurate.

Ketone monitoring also is becoming recognized as a tool for nutritionists or health care professionals to monitor lipid metabolism during dieting. Several studies show that breath acetone concentrations represent lipid metabolism during a calorie deficit. Obesity has become increasingly prevalent and has now reached epidemic levels. It is consequently of great concern to healthcare professionals. Much effort has been invested in treating obesity and promoting healthy weight loss programs for obese individuals. For treatment of obesity, a sensor that measures fat burning is needed to adjust weight management plans to individual physiology. A non-invasive, inexpensive, simple-to-use acetone sensor would be an appropriate tool for nutritionists, physicians, and the general public who seek to monitor fat metabolism.

Some systems for measuring analytes in air operate on electrochemical principles (see, e.g., U.S. Pat. No. 5,571,395, issued Nov. 5, 1996, to Park et al.), and some operate by infrared detection (see, e.g., U.S. Pat. No. 4,391,777 issued Jul. 5, 1983, to Hutson). U.S. Pat. No. 6,658,915, issued Dec. 9, 2003, to Sunshine et al., describes using chemically sensitive resistors to detect airborne substances and requires the use of an electrical source.

U.S. Pat. No. 4,935,345, issued Jun. 19, 1990 to Guilbeau et al., describes the use of a single thermopile in liquid phase chemical analysis. However, the thermopile sensor is limited to measuring a single analyte and only a single reactant is present on the thermopile. This sensor operates in the liquid phase. Each of the foregoing patents is hereby incorporated herein by reference as if fully set forth herein.

A fast, inexpensive, non-invasive method of measuring analytes in fluids, particularly gas, is needed.

SUMMARY

In one embodiment according to an aspect of the present invention, a sensor is provided for detecting at least one analyte in a gas. The sensor comprises a thermoelectric sensor having a layer of at least one analyte interactant and at least one thermopile.

Optionally, a microprocessor may be provided in electrical communication with or otherwise operatively coupled to the thermopile.

In another option, a collection device is provided for collecting the gas containing the analyte.

The analyte is brought into contact with the interactant and produces or consumes heat that is transmitted to the thermopile, which produces a voltage difference. The optional microprocessor correlates the voltage difference to the concentration of the analyte and indicates the presence of the analyte.

Optionally, the interactant is selected from a chemical reactant, catalyst, adsorbent, absorbent, catalyst, binding agent, a phase change, aptamer, vaporization agent or a combination thereof.

In another embodiment, the sensor can have multiple thermopiles, each having the same or different interactants, which are each independently connected to or otherwise operatively coupled to the microprocessor, thereby providing a display of single or multiple analytes.

In another embodiment, the interactant is selected from sodium hypochlorite, hypochlorous acid, sodium monochloroisocyanurate, monochloroisocynanuric acid, sodium trichloroisocyanurate, trichloroisocyanuric acid, nitrosyl chloride, chloroform, chloroform in the presence of a base, protonating agents, nitrosyl chloride, or a combination thereof.

In another embodiment, the sensor's microprocessor also communicates with an electronic display, alarm, noise maker, other output or a combination thereof.

In another embodiment, the analyte is acetone, whose presence indicates the presence of ketones in the bloodstream.

In another embodiment, the interactant is specific for alkanes, whose presence may indicate various pathologies, such as breast cancer and transplant rejection.

In another embodiment, the thermopile is fabricated from bismuth/antimony, other metals, alloys, semiconductor materials, or liquid thermoelectric materials.

In yet another embodiment, the analyte interactant comprises biologically active materials comprising cells, cell organelles, micro-organisms or genetically modified organisms.

In another embodiment, compounds present in the air stream other than the analyte of interest facilitate the production or consumption of heat.

In another embodiment, the gas stream is replaced by a liquid.

In accordance with another aspect, a method is provided for detecting an analyte by a thermoelectric sensor. The method comprises providing a thermoelectric sensor, wherein the sensor has a layer of at least one analyte interactant that when combined with the analyte gives off or consumes heat, and at least one thermopile to which the heat change is transferred, which then registers a voltage difference. The method further comprises contacting the interactant of the thermoelectric sensor with the analyte, and indicating the presence of the airborne analyte.

The providing of the thermoelectric sensor can also comprise providing an analyte interactant specific for acetone and the provided display indicates the presence of acetone, whereby the burning of fat is indicated.

In another embodiment, the provided thermoelectric sensor has multiple thermopiles, each having the same or different analyte interactants and each being connected to or otherwise operatively coupled to the microprocessor, e.g., by two leads, and the presence of one or multiple airborne analytes are indicated.

In another embodiment, indicating the presence of the airborne analyte also comprises indicating the concentration of the analyte.

In still another embodiment, there is a sensor for detecting at least one ketone in expired air and the occurrence of a fat-burning state. This sensor comprises a capture apparatus, a thermoelectric sensor, a microprocessor and a display. The sensor comprises a layer of at least one interactant specific for the ketone and at least one thermopile having a first and a second contact pad. The microprocessor is attached to first ends of a first lead and a second lead, the first lead having a second end attached to the first thermopile contact pad and the second lead having a second end attached to the second thermopile contact pad. The display is connected to the microprocessor for indicating the presence or quantity of at least one ketone.

In another embodiment, the interactant is selected from a chemical reactant, catalyst, adsorbent, absorbent, vaporization agent or a combination thereof. Optionally, the sensor has multiple thermopiles, each in contact with the same or different interactants, which are each independently connected to the microprocessor via two leads. The interactant preferably is selected from sodium hypochlorite, hypochlorous acid, sodium monochloroisocyanurate, monochloroisocynanuric acid, sodium trichloroisocyanurate, trichloroisocyanuric acid, nitrosyl chloride, chloroform, chloroform in the presence of a base, protonating agents, nitrosyl chloride, or a combination thereof. The microprocessor also communicates with an electronic display, alarm, noise maker, other output or a combination thereof. The analyte can be or comprise acetone, whose presence indicates the presence of ketones in the bloodstream. The thermopile can utilize bismuth/antimony, other metals, alloys, semiconductor materials, or liquid thermoelectric materials. The analyte interactant can be or comprise biologically active materials comprising cells, cell organelles, micro-organisms or genetically modified organisms. Optionally, the sensor comprises at least one compound present in the air stream, other than the analyte of interest, which facilitates the production or consumption of heat.

In other embodiments, the microprocessor further is preprogrammed for a location of at least one thermopile and for a correlation of the voltage change with the location. The interactant is selected from a chemical reactant, catalyst, adsorbent, absorbent, vaporization agent or a combination thereof. Multiple thermopiles, each having the same or a different interactant, each independently transmits voltages to the microprocessor. The signal output device can be an electronic display, noise maker, alarm, other output or a combination thereof. The thermopile can be fabricated from bismuth/antimony, other metals, alloys, semiconductor materials, or liquid thermoelectric materials. The analyte interactant can be or comprise biologically active materials such as cells, cell organelles, micro-organisms or genetically modified organisms. Optionally, compounds present in the air stream other than the analyte of interest facilitate the production or consumption of heat.

In one embodiment there is an apparatus for detecting analytes in fluids comprising a conduit for channeling said analyte containing fluid past a two or more analyte reaction surfaces in series, said reaction surfaces being coated with an interactant that takes up said analyte and reacts with it to produce a physical reaction that can be sensed; a plurality of sensors disposed to detect said physical reaction; and at least one replenishment region disposed between said at least two analyte reaction surfaces, whereby analyte concentration in said fluid that was depleted by said take up replenished.

The fluid can be a gas such as air or human breath or a liquid such as water.

The analytes can be found in the human breath such as acetone, isoprene, alkanes, alcohols, such as ethanol, ammonia, benzene, acetaldehyde, acetonitrile, methylene chloride, methyl ethyl ketone, toluene, medications and reflux.

Interactants can be trichloroisocyanuric acid, a group of ethanol reactants consisting of or comprising chromium trioxide, alcohol dehydrogenase and alcohol oxidase, a group of ammonia reactants consisting of or comprising hypochlorous acid and barium hydroxide, a group of inorganic reactants consisting of or comprising halogenated isocyanuric acid, trichloroisocyanuric acid, hypochlorous acid, sodium hypochlorite, sodium di/mono isocyanurate, chloroform with a base, nitrosyl chloride, and chromium trioxide or, in general, a group consisting of or comprising a chemical reactant, catalyst, adsorbent, absorbent, vaporization agent or a combination thereof.

Still other interactants that can be used can be selected from a group of hydrogenation reactants consisting of Raney nickel and platinum, a group of adsorbents consisting of activated charcoal and activated carbon impregnated with halogen compounds, or an organic enzyme, such as acetoalcohol oxidase.

Sensors can be selected from a group of sensors consisting of thermistors, thermocouples, thermopiles, ion sensors, and radiation sensors.

The replenishment region can comprises a portion of the conduit having non-reactive walls disposed between said reaction surfaces or further having an obstruction disposed therein.

In another embodiment, the apparatus may further have at least one temperature compensating reference sensor. In one embodiment the reference sensor is selected to respond to heating or cooling by the fluid in the same amount as said physical condition sensors.

In one embodiment, the apparatus conduit is rectangular with sensors on top and bottom with a selected spacing.

BRIEF DESCRIPTION OF THE DRAWINGS

The invention will now be described in more detail with reference to preferred embodiments, methods and forms of the invention, given only by way of example, and with reference to the accompanying drawings, in which.

DETAILED DESCRIPTION

Figure 1:
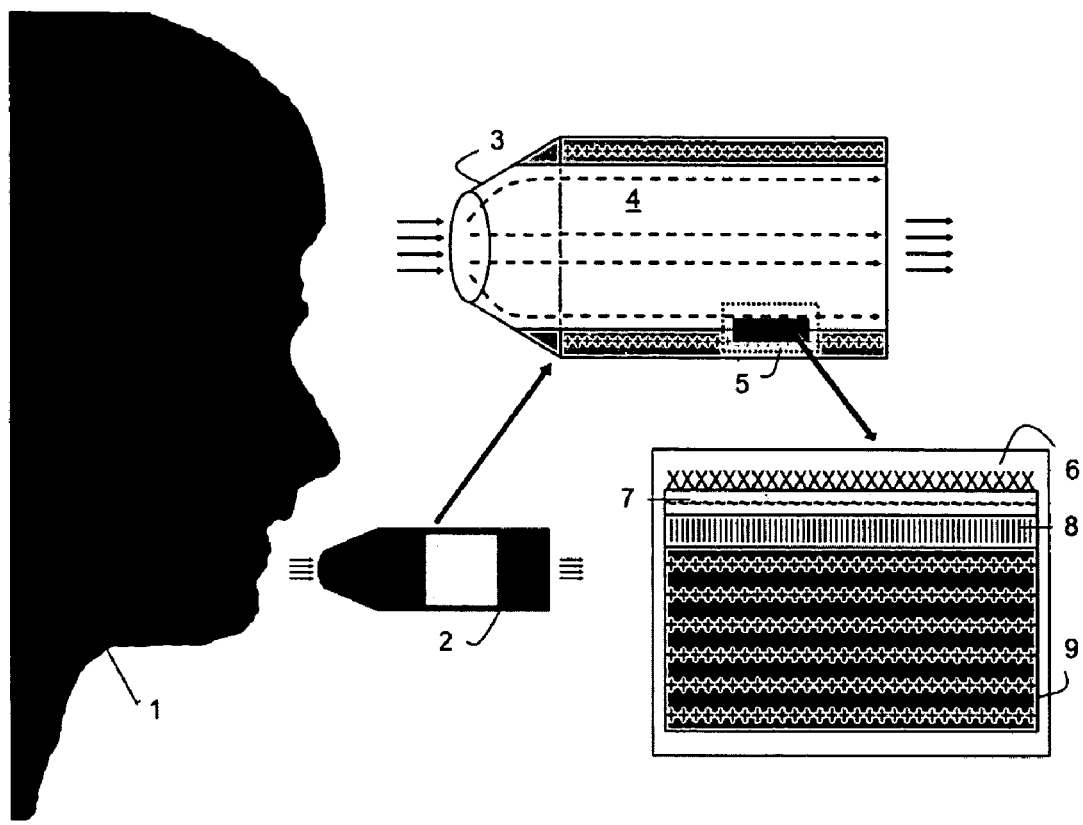
FIG. 1 shows is a composite illustration of sensor details and a device in use.

A measuring device is required to determine the concentrations of biochemical or chemical substances expired by the body or contained within other gas. Disclosed herein is a thermoelectric gas analyzer. It is noninvasive and provides a representation of analytes in the bloodstream without requiring direct access to the bloodstream. "Gas" as the term is used herein, incidentally, is used in its broad but common meaning with the field, for example, to include not only pure gas phases but also vapors, non-liquid fluid phases, gaseous colloidal suspensions, solid phase particulate matter or liquid phase droplets entrained or suspended in gases or vapors, and the like.

More that 200 analytes have been identified in human breath. Examples include but are not limited to pentane and other alkanes, isoprene, benzene, acetone and other ketones, alcohols such as ethanol, methanol, isopropanol, ammonia, reflux, medication, and substances which interfere with common alcohol detection systems such as acetaldehyde, acetonitrile, methylene chloride, methyl ethyl ketone, and toluene. Some analytes are in vapor form while others may be in particle form.

A thermocouple is a device where one material is fused to a disparate material at both of its ends. The materials usually are conductors such as metals, alloys, or liquid thermoelectric materials that may or may not contain dopants. The point of contacts are called thermoelectric junctions. A temperature gradient between the two thermoelectric junctions causes electrons to travel toward the colder region which causes a potential difference between the junctions. This is called the thermoelectric effect.

When a fluid comes in contact with a surface, there in a no-slip boundary condition and the velocity at the surface is therefore zero. The velocity therefore varies between zero and the bulk velocity. The distance between the surface and the point at which molecules are traveling at 99% of the bulk velocity is known as the hydrodynamic boundary layer. As the distance from the leading edge increases, the thickness of the hydrodynamic boundary layer increases. If the fluid is passing through a conduit, the hydrodynamic boundary layer is limited by the dimensions of the conduit such as the height.

If the surface is coated with a chemical, then a concentration boundary layer will form. As with the hydrodynamic boundary layer, the thickness of the concentration boundary layer will increase as a function of distance from the leading edge. Therefore, the flux to the surface decreases rapidly along the length of the conduit with maximum flux occurring at the leading edge. The diminishing flux is an important consideration if it is necessary to react the analyte with a chemical immobilized at the surface.

One way to increase the flux at the surface is to interrupt the growth of the concentration boundary layer. If the chemical is immobilized in a discontinuous fashion such that the chemical is immobilized for a certain distance and followed thereafter by some interruption, said interruption including but not limited to a non-reactive surface of the same or a greater distance, then the concentration boundary layer thickness will decay. Thereafter, if chemical is present at the surface, the concentration boundary layer will begin to grow again. In this way, the flux to the surface is relatively high at each point where there is chemical present. Using this manner of chemical patterning, the flux to the surface can greatly surpass the flux that would be achieved if the entire surface had been coated with chemical without the interruptions and discontinuities.

There are other ways by which the concentration boundary layer can be interrupted. For instance, if the fluid flow changes direction, then both the hydrodynamic and concentration boundary layers will be interrupted. This could happen using a coiled flow path.

Another way to interrupt the concentration boundary layer is to place an obstruction immediately following the immobilized chemical. This obstruction would force the streamlines to change direction and therefore cause turbulence. The boundary layers would reform when the fluid comes in contact with a smooth surface.

Another way to interrupt the concentration boundary layer is to immobilize chemical throughout the chamber, but to inactivate the chemical at the appropriate locations. For instance, if the chemical can be inactivated by exposure to UV light, an appropriate photo-mask can be designed to achieve this.

This voltage is described as follows: $V = n \cdot S \cdot \Delta T$ where V is the voltage, n is the number of thermocouples, S is the Seebeck coefficient of the two metals, and $\Delta T$ is the temperature difference between the sensing and reference junctions. Amongst pure metals, antimony and bismuth have the highest Seebeck coefficient. Thermocouples that are connected in series are called thermopiles.

In one embodiment, a thermoelectric sensor works as follows. The sensing junctions and not the reference junctions of a thermocouple or thermopile are coated with some substance. The substance is selected such that it interacts with an analyte of interest in an enthalpic process.

Preferably but optionally, both the reference and sensing junctions are coated with a non-interactive substance that helps to equalize the thermal load on both of these junction sets. For example, if an enzyme such as alcohol dehydrogenase is entrapped within a gel matrix, the gel matrix without the enzyme might be placed on the reference junctions and that gel containing the enzyme on the sensing junctions. In another case, both the reference and sensing junctions are coated with a substance like silicone grease. Over the sensing junctions, the silicone grease adheres interactants that are in particle form such as trichloroisocyanuric acid.

Optionally, the reference junctions may be coated with an interactive substance that is different from the interactive substance that is placed on the sensing junctions. In one embodiment, the analyte interacts with the reference junction interactant in an endothermic process and with the sensing junction interactant in an exothermic process.

Optionally, the legs of the thermopile or that area between the reference and sensing junctions may be coated with an interactive substance. The heat that is consumed or generated in this area could be transferred to the junctions whereas the temperature difference is proportional to the output voltage of the thermopile.

The interactant may be immobilized on the sensing junctions directly. If, however, the interactant can cause corrosion or other negative impacts to the thermopile materials which will affect the longevity of the device, other embodiments may be better suited. Preferably, the interactant is immobilized on the side of the substrate opposite the thermopile in such a way that the heat will be transferred preferentially to the sensing junctions. In thin isotropic materials, this is achieved by immobilizing the chemical directly over the sensing junctions.

Optionally, and advantageously, the substrate can be folded so as to allow for creation of a catheter-type device.

Generally speaking, the reference junctions compensate for changes in the temperature of the gas stream. If the reference junction temperature were fixed by placing the junctions over a heat sink or insulating them, for example, then a non-interaction effect such as a change in the gas stream temperature would cause a temperature difference between the reference and sensing junctions. In medical applications, this typically is a concern. When the expired patient breath passes over the sensor, the thermopile will experience a non-interaction based temperature change merely due to the fact that expired breath is close to body temperature which is close to 37° C. If the sensor is originally contained in an environment which is at 37° C., this may not be an issue. If the thermopile was at room temperature originally and the temperature of the reference junctions was fixed, then the sensor would register a voltage that is proportional to a temperature change between body and room temperature. However, if both the reference and sensing junctions are exposed to the gas stream, then the thermopile will register a temperature change of zero because of the thermopile's inherent common mode rejection.

When a gas or breath comes in contact with the thermopile, the enthalpic process occurs, the cumulative effect of which is that net heat is generated or consumed on the sensing junctions. This heat generation or consumption causes a temperature difference between the sensing and reference junctions. The output voltage is proportional to the temperature difference between the junction sets, which temperature difference is related to the heat generated or consumed by the analyte interactions, which in turn is related to the amount of the analyte.

The gas can come in contact with the thermopile in different ways. In one embodiment, the analyte diffuses from the gas to the sensor. In another embodiment, the analyte is convected directly onto the sensor. In yet another embodiment, the analyte is convected across the sensor and diffusion occurs to bring the analyte in contact with the sensor.

The enthalpic process occurs due to the interaction of the analyte and the reactive substance(s). The analyte-interactant produces or consumes heat by any of a variety of ways, including but not limited to chemical reaction, adsorption, absorption, binding effect, aptamer interaction, physical entrapment, a phase change, or any combination thereof. Biochemical reactions such as DNA and RNA hybridization, protein interaction, antibody-antigen reactions also can be used to instigate the enthalpic process in this system.

Aptamers, as those skilled in the art will understand, are specific RNA or DNA oligonucleotides or proteins which can adopt a vast number of three dimensional shapes. Due to this property, aptamers can be produced to bind tightly to a specific molecular target. Because an extraordinary diversity of molecular shapes exist within the universe of all possible nucleotide sequences, aptamers may be obtained for a wide array of molecular targets, including most proteins, carbohydrates, lipids, nucleotides, other small molecules or complex structures such as viruses. Aptamers are generally produced through an in vitro evolutionary process called "systematic evolution of ligands by exponential enrichment" (SELEX). The method is an iterative process based on selection and amplification of the anticipated tight binding aptamer. The start library for selection of aptamers contains single stranded DNA oligonucleotides with a central region of randomized sequences (up to 1015 different sequences) which are flanked by constant regions for subsequent transcription, reverse transcription and DNA amplification. The start library is amplified by PCR and transcribed to an RNA start pool by T7 transcription. Target specific RNA is selected from the pool by allowing the pool to interact with the target molecule, only tight binding RNA molecules with high affinity are removed from the reaction cycle, the tight binding RNA molecules are reverse transcribed to cDNA and amplified to double stranded DNA by PCR. These enriched binding sequences are transcribed back to RNA which is the source for the next selection and amplification cycle. Such selection cycles are usually repeated 5-12 times in order to obtain only sequences with highest binding affinities against the target molecule.

Interactants can be adsorbents including but not limited to activated carbon, silica gel, and platinum black. Preferably, the adsorbent can be impregnated with another species that reacts with the analyte following the adsorption.

Interactants can also be chemicals or chemical reactants. Suitable chemicals that interact with acetone include but are not limited to halogenated compounds, sodium hypochlorite, hypochlorous acid, sodium monochloroisocyanurate, sodium dichloroisocyanurate, monochloroisocyanuric acid, dichloroisocyanuric acid, and trichloroisocyanuric acid. Alcohol can interact with a chemicals such as chromium trioxide ($CrO_3$) or enzymes such as alcohol dehydrogenase, alcohol oxidase, or acetoalcohol oxidase.

Optionally, the interactant may not directly interact with the analyte, but a byproduct of the interactant and some other compound in the gas can produce a different interactant with which the analyte reactants. For example, trichloroisocyanuric acid can react with water to form hypochlorous acid, which engages in an enthalpic reaction with acetone. Vapor phase reactions are sometimes limited because reactions in aqueous solution typically involve acid or base catalysis.

Therefore, in the vapor phase, the presence of a catalyst, such as a protonating agent, may be critical to allow the interactant and analyte to interact.

Optionally, interactants can also be hydrogenation reagents. For acetone, Raney nickel and platinum catalysts are suitable interactants.

The analyte can also interact with materials from living systems or living systems themselves. Examples include but are not limited to microorganisms, cells, cellular organelles and genetically modified versions thereof. These living systems engage in metabolic processes to sustain life which involve energy exchange and therefore heat consumption or generation. Some chemical analytes such as toxins or pathogens kill or damage cells or impair organelle function. If the living material is immobilized on the sensing junctions of a thermopile, therefore, the change in heat generated or consumed is related to the number of living cells which can be related to the presence of a toxin or pathogen.

More than one interaction can also occur simultaneously or sequentially. This occurs if multiple interactants are immobilized on the sensing portion of the device. In this case, the net enthalpy of these interactions dictates the response of the device. A non-zero net enthalpy causes a temperature change on the sensing junctions relative to the reference junctions, which temperature change can be quantified by measuring the output voltage.

Even if only one interaction occurs, the chemistry may be selected such that the products of the initial reaction act as reactants during secondary interactions with the analyte or other substances which can amplify temperature changes.

Optionally, the interactant may be selected such that the interaction with the analyte involves interaction with other substances in the gas, such as water, oxygen, or another analyte.

Figure 2:
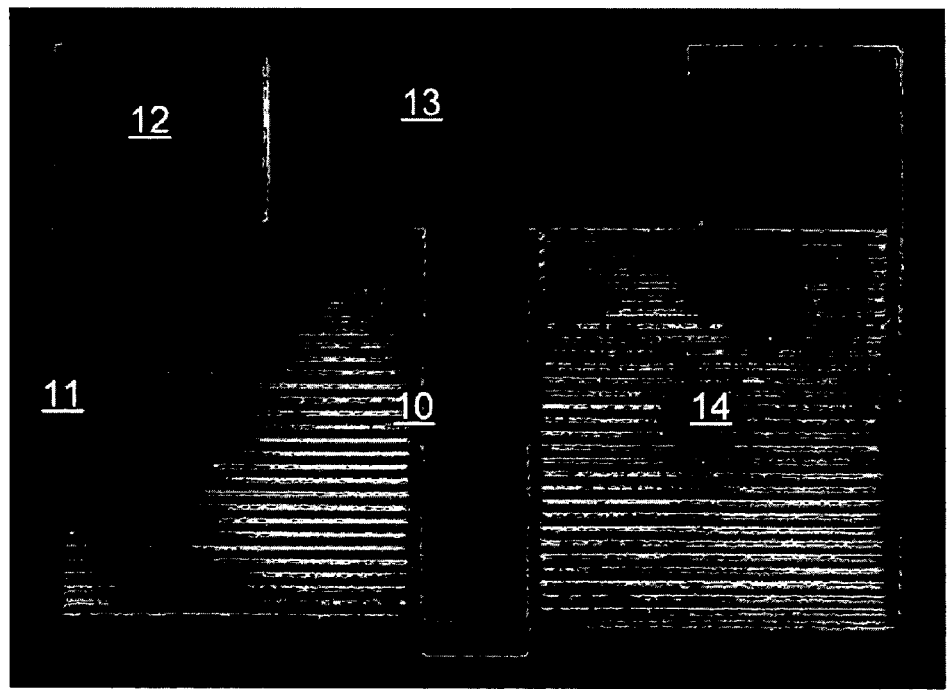
FIG. 2 is a schematic top view of a rectangular thermopile suitable for use in FIG. 1.

Thermopile geometry varies and can be optimized to meet different needs or design objectives. FIGS. 1 and 2 show different thermopile geometries: rectangular and circular. The rectangular embodiment is preferred in situations where, for instance, there is flowing gas over the thermopile. The energy consumed or generated at the sensing junctions can be convected downstream instead of to the reference junctions. In the latter case, the signal would be slightly masked. The circular embodiment is preferred in systems, for example, where the interactant is best immobilized as a droplet or other spherical form. Additionally, the circular geometry provides symmetry to the device where the reference junctions are all equally distributed from the enthalpic process. In these embodiments, the cumulative voltage generated by the individual thermocouples is measured as the thermopile contact pads.

In one embodiment, multiple thermopiles may be linked in arrays. Several thermopiles can have the same interactant to detect the same analyte. Their voltages could be averaged by a microprocessor with the result that net effect of noise is reduced. Alternatively, each of several thermopiles may be coated with a different interactant so as to more selectively detect a single analyte.

In other cases, measuring multiple analytes may be desirable. In the presently preferred embodiments, each thermopile within the array may be coated with a different material such that selectivity of several analytes is determined by the different interactions. The response of the individual thermopiles is determined by the individual thermopile voltage response which creates an overall profile. This profile or pattern will be characteristic of a specific analyte or analytes of similar chemical family and can therefore be used to identify at least one analyte.

The voltage output of the thermopile can be measured directly or by use of a microprocessor. The microprocessor may report the voltage or may convert the voltage to a concentration or other interpretable signal. This conversion may be programmed by use of a calibration curve, look-up table, or other method.

Optionally, the microprocessor may be used to provide feedback, which feedback can be programmed to analyze the status and transmit commands to operate something like a drug delivery device.

The thermopile voltage will vary as a function of the temperature difference which will likely change through the course of the enthalpic interaction. For instance, certain chemical reactions propagate and get increasingly more exothermic. Additionally, depending on the flow conditions, the output voltage may change. Therefore, it may be necessary for the microprocessor to process the signal. Examples of the types of responses that have been found meaningful here are the peak voltage, the slope of the voltage versus time curve, and the area under the voltage versus time curve. Depending on the time over which the analyte interacts with the interactant, different signals may be more indicative of the analyte concentration.

The output of the microprocessor or the thermopile can be quantitative or qualitative, depending on the application, use, design objectives, etc. For example, an acetone sensor designed for pediatric patients may have colored indicators of the seriousness of diabetic ketoacidosis. However, for physicians, the exact concentration of acetone may be displayed.

The thermopile can be integrated within a microfluidic gas analysis device. Microfluidic devices have gained significant interest recently due to their ability to perform multiple processes in very short time intervals and in very little space. The thermopile is well suited for use in a microfluidic gas analyzer because it is easily miniaturized.

The voltage output of the thermopile is proportional to the Seebeck coefficient of the metals, the number of thermocouples, and the temperature difference between the sensing and reference junctions. One way to increase the thermopile signal is to increase the number of thermocouples.

For this to be effective, the sensing junctions of the added thermocouples should be immobilized with additional chemical. This way more analyte will be consumed in the enthalpic process, which could be a reaction. There are different ways by which the thermopile sensor can be designed to optimize consumption.

Preferably, but optionally, both the reference and sensing junctions are coated with a non-interactive substance that helps to equalize the thermal load on both of these junction sets.

Preferably, but optionally, the flow is directed in such a way that all of the analyte in the entering gas stream flows over the junctions of the thermopile. In this way, fluid flow over the legs of the thermopile between the sensing and reference junctions is minimized. This is particularly important when a bolus of fluid is injected into or exposed to the device in which case the number of molecules available for reaction is limited.

In one embodiment, the thermopile is insulated with the metals facing the insulation and the substrate left exposed. On the substrate and over the legs of the thermopile, barriers are created, said barriers serving as channel walls by which to direct fluid flow over the junctions (both reference and sensing). The placement of the channel walls over the legs of the thermopile does not affect the signal as the thermopile response is proportional to the change in temperature between the reference and sensing junctions not any intermediate temperature differentials.

In a preferred embodiment and particularly if the surface reactions are highly exothermic, the channels can be created such that the reference junctions are contained within channels disparate from those containing the sensing junctions. A possible advantage of this embodiment is that lateral heat transfer from the sensing to reference junctions will be minimized. Additionally, if the channels are designed in such a way that the reference junction channels are positioned at the start and end of the entire flow path, the temperature compensation is improved. In other words, the fluid flowing over the sensing junctions may experience an increase in temperature due to the convective heat transfer. Therefore, it is possible that the temperature of the gas will increase as a function of distance through the channels. In this case, therefore, it is desirable that the reference junctions exist at the start and end of the flow path.

In a preferred embodiment, the sensing and reference junctions are placed in an alternating fashion along the length of the conduit. This may be useful if the flow conditions are such that turbulent flow is expected. In this case, both the sensing and reference junctions would experience the same effect which would help to reduce the effect of thermal noise which may be higher than normal under turbulent flow conditions due to the presence of fluid eddies, etc.

Preferably, the chemical is deposited immediately after the leading edge. Assuming an instantaneous reaction, the flux of analyte to the surface is directly proportional to the bulk concentration and square root of the distance from the leading edge and inversely proportional to the square root of the velocity. Immobilizing chemicals over large length so the sensor thus becomes inefficient at some point.

In one embodiment, there is a thermopile at the top and bottom of the conduit. The thermopile at the top and the one at the bottom will both have chemical immobilized and the fluid will be exposed to both devices. There will be flux to both the top and bottom devices which will at least double the signal.

In another embodiment, the entering flow stream should be divided and directed over a different set of electrically coupled reference and sensing junctions. In this way, the velocity over the immobilized chemical will be less. As the velocity decreases, the analyte has more time to diffuse to the surface as diffusion transport will dominate over convection transport.

The interactant may be immobilized on the sensing junctions directly. If, however, the interactant can cause corrosion or other negative impacts to the thermopile materials which will affect the longevity of the device, other embodiments may be better suited. Preferably, the interactant is immobilized on the side of the substrate opposite the sensing junctions in such a way that the heat will be transferred preferentially to the sensing junctions. In thin isotropic materials, this is achieved by immobilizing the chemical directly over the sensing junctions.

In one embodiment, multiple thermopiles may be linked in arrays. Several thermopiles can have the same interactant to detect the same analyte. Their voltages could be averaged by a microprocessor with the result that net effect of noise is reduced. Alternatively, each of several thermopiles may be coated with a different interactant so as to more selectively detect a single analyte.

In other cases, measuring multiple analytes may be desirable. Here, each thermopile within the array may be coated with a different material such that selectivity of several analytes is determined by the different interactions. The response of the individuals thermopiles which is determined by the individual thermopile voltage response which creates an overall profile. This profile or pattern will be characteristic of a specific analyte or analytes of similar chemical family and can therefore be used to identify at least one analyte.

Figure 21:
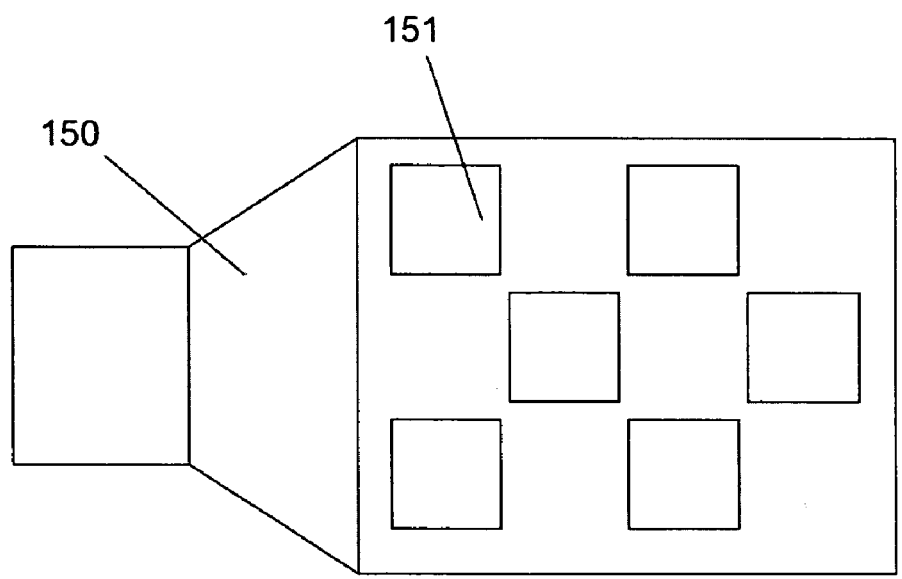
FIG. 21 shows a possible layout of a device using multiple thermopiles.
Figure 22:
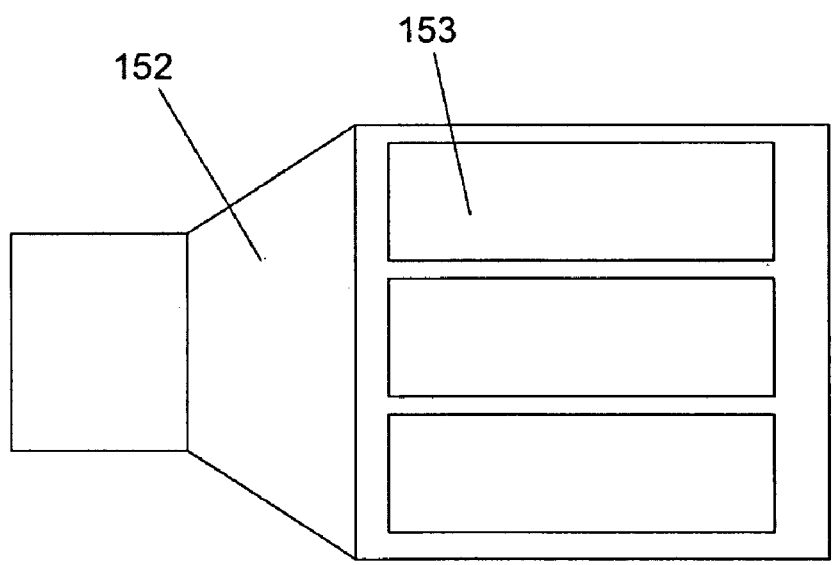
FIG. 22 shows a possible layout of a device using multiple thermopiles.

If multiple devices are used either to more selectively identify the analyte or to reduce the error of a single device, then there are some geometry considerations that are important. For instance, the devices should all be placed side by side as close to the leading edge as possible. FIG. 22 shows a possible embodiment of a device 152 containing multiple sensors 153 where the sensors are placed side by side close to the leading edge of the device. If this is not possible, then the devices should be placed with gaps between them. The exact geometry can vary from one setup to the next. One may place the devices in a chess-board like pattern because the formation of the boundary layer is streamline-specific. FIG. 21 shows another setup of a device 150 where multiple sensors 151 are placed in a chess-board like fashion.

EXAMPLES

Example 1

FIG. 1 shows is a composite illustration of sensor details and a device in use. A user 1 blows into device 2 through a mouthpiece 3. The breath passes through the mouthpiece 3 into a conduit 4 where a sensor 5 is located. The analyte in the breath diffuses to the surface of the sensor where an interactant 6 engages the analyte in an enthalpic process. The heat generated (or consumed) from this process is transferred through a substrate 7 to sensing junctions of the thermopile 8 thus raising (or lowering) the temperature of the sensing junctions. This change in temperature produces a change in the voltage produced by the sensor 5. The thermopile is thermally insulated from the ambient by a suitable insulator 9.

The conduit 4 may be cylindrical, rectangular or any of a variety of shapes that allow the analyte to reach the sensor 5. The mouthpiece 3 may be detachable and replaceable. Alternately the conduit may be as narrow as a mouthpiece. For situations in which the analyte is transferred to the thermopile purely by diffusion, the conduit may only consist of an overlying shelter to protect the sensor from particles such as dust.

Example 2

FIG. 2 is a schematic top view of a rectangular thermopile suitable for use in FIG. 1. The thermopile consists of two dissimilar conductors that are deposited on a substrate 13 and shown as alternating strips of conductors 14. The conductors are patterned such that there are two sets of junctions between conductors, the sensing junctions 10 and the reference junctions 11. One of the conductors spans the distance between any reference and sensing junction, which are all in series electrically. As a result, the voltage between the contact pads 12 is the sum of the EMFs of the individual thermocouples which are each made up of a single sensing junction (from the sensing junction set 10) and a single reference junction (from the reference junction set 11). Normally thermopiles are arranged to have an equal number of each. As illustrated, there are about 60 of each.

Figure 3:
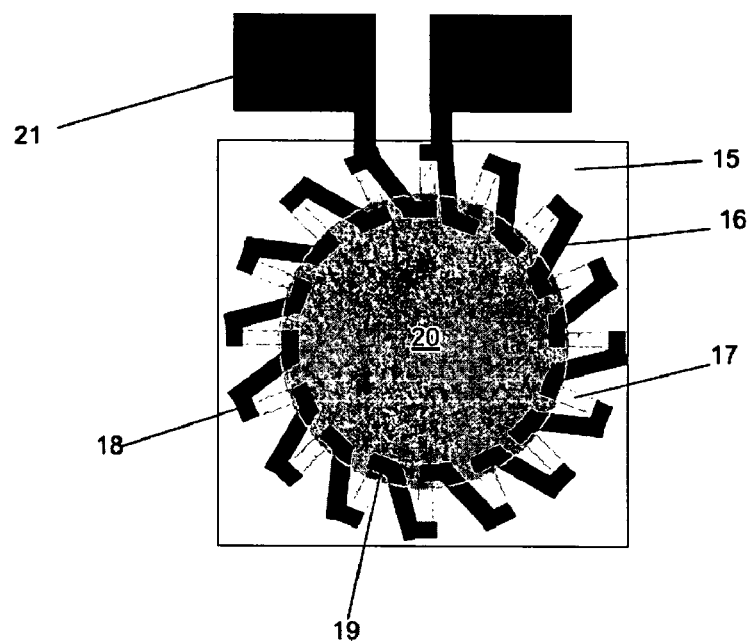
FIG. 3 is a schematic showing a circular thermopile.

FIG. 3 is a schematic showing a circular thermopile. Thermopile conductors will be deposited onto a substrate 15 on which a first conductor material 16 and a second conductor material 17 are deposited to form reference junctions 18 and sensing junctions 19. The interactant 20 would be deposited proximate to the sensing junctions 19. The voltage can be measured by use of the contact pads 21.

Laboratory prototype thermopiles were constructed with the geometry illustrated in FIG. 2. Bismuth metal was first evaporated onto a polyimide Kapton® thin film substrate through a mask. Once the bismuth deposition was complete, the substrate-mask combination was removed from the metal evaporator. The bismuth mask was removed and an antimony mask clamped to the substrate in such a manner that the antimony deposition would complement the bismuth deposition layer to form the thermopile. Once the antimony deposition was complete, a thin layer of bismuth was deposited on top of the antimony. It has been determined empirically that the thermopile yield is improved significantly. Nevertheless, it must be noted that certain commercially available thermopiles demonstrate less background noise than the prototypes described herein.

To make electrical contact to the thermopile contact pads 12, thin copper wire was attached through the use of a silver bearing epoxy paint.

Figure 4:
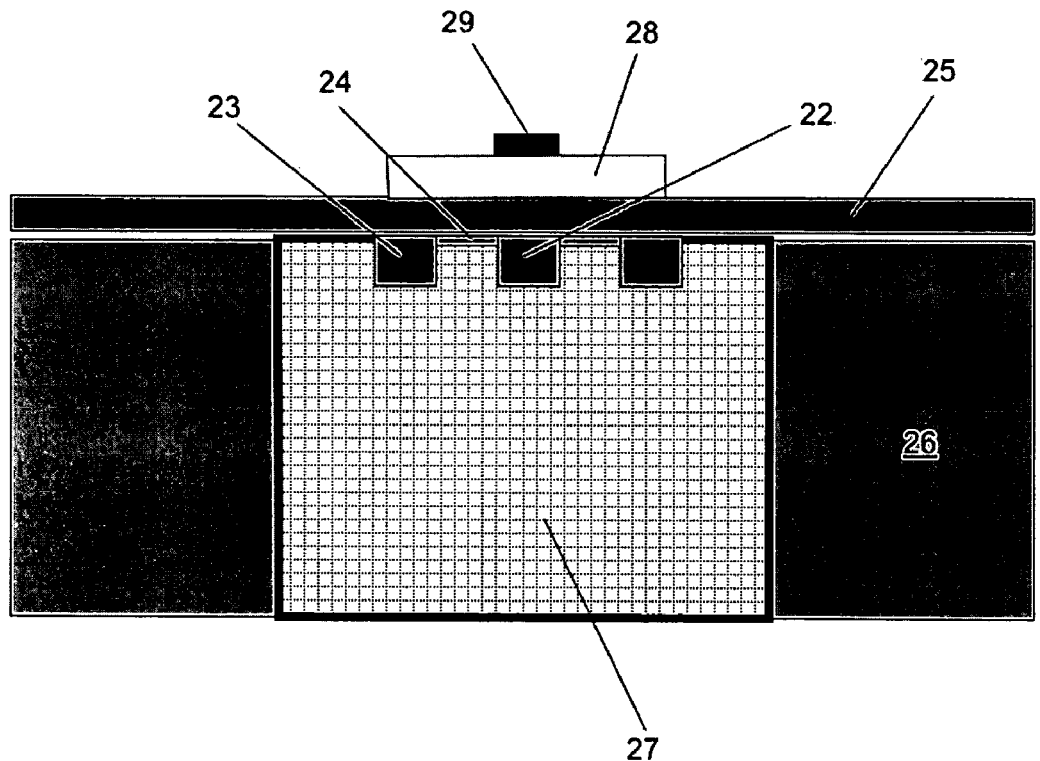
FIG. 4 shows a side cross-section of a thermopile sensor as it was installed in a housing.

FIG. 4 shows a side cross-section of a thermopile sensor as it was installed in a housing. Illustrated are sensing junctions 22, reference junctions 23, and thermopile conductor legs 24 connecting the junctions deposited on deposited on a substrate 25 as described above. For the prototypes, the substrate was placed on a plastic annulus 26 approximately 25 mm in diameter with the metals facing inside the annulus into cylindrical region 27 and the substrate 25 facing the external environment. The cylindrical region 27 was filled with polyurethane insulation. On the other side of the substrate, silicone grease 28 (not shown to scale) was placed such that it covers the area over the entire thermopile. An interactant 29 was placed over the sensing junctions 22 of the thermopile. The copper wires (not shown) protruded from beneath the substrate 25. The advantage of this approach is that the metal of the thermopile are not exposed to the external environment, but the thermal path to the interactant 29 is longer.

Figure 5:
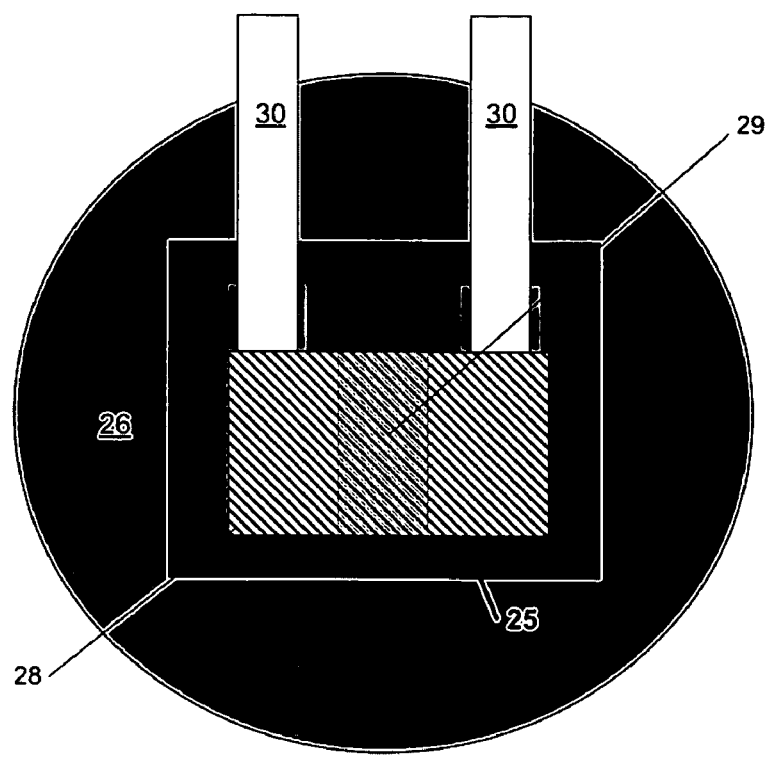
FIG. 5 illustrates the top view of the sensor illustrated in FIG. 4.

FIG. 5 illustrates the top view of the sensor illustrated in FIG. 4, showing the substrate 25 placed on a plastic annulus 26 with the metals facing the inner cylinder of the annulus. Copper wires 30 are electrically connected to the contact pads of the thermopile. The silicone grease 28 is placed over the entire thermopile and the reactant 29 is placed only over the sensing junctions.

For this type of sensor, the ideal chemical reactant is regenerative (not consumed), highly selective to the analyte of interest, and non-toxic, has a long shelf life, and engages in a highly exothermic or endothermic reaction with the analyte or analytes.

This setup has been tested with sodium hypochlorite, hypochlorous acid, and trichloroisocyanuric acid. In this case, the chemical reactants are not in direct contact with the thermopile metals 14. Rather, the chemicals are immobilized on the substrate 13 opposite the thermopile metals 14. The disadvantage of this configuration is that heat must be transferred through the substrate. However, the substrate is extremely thin and therefore the resistance to heat transfer is low. The advantage is that there is no effect of the interactant on the thermopile and also the interactant can be removed and replaced without impact to the thermopile.

Referring also to FIG. 2, the area of the substrate 13 surface that was vertically above the entire surface of the thermopile was coated with silicone vacuum grease to keep the thermal load on both the reference and sensing junctions approximately constant thereby allowing the time constant of the two sets of junctions to be equal. Initially, double-stick cellulose acetate tape was utilized instead of the silicone grease. However, it was determined empirically that acetone reacts with the adhesive portion of the tape, thereby causing a series of competing reactions. A precise volume of trichloroisocyanuric acid was dusted onto the silicone grease over only the portion of the substrate 13 which was vertically above the sensing junctions 10 in precise geometrical fashion by use of a rectangular mask.

Once a thermopile unit is created with the chemical immobilized and wires attached, it should be housed in a device that will allow for an interface with the breath or analyte of interest. In this embodiment, a laminar flow chamber was constructed. To decrease the chances of turbulent flow, sharp edges were removed from the system. A rectangular conduit was selected with a top and bottom piece. The height was made extremely small, again to minimize the chances of turbulent flow.

Two circular holes of different diameters were drilled in the top plate of this conduit trough the top. One hole allowed the gas with the analyte to enter the chamber. The second hole tightly fit the thermopile sensing unit with the chemicals facing downward and into the slit. It is believed that this allowed air with the desired analyte to enter the flow chamber through the small hole, achieve fully developed laminar flow through the course of the conduit and interact with the chemical on the downward facing thermopile.

Figure 6:
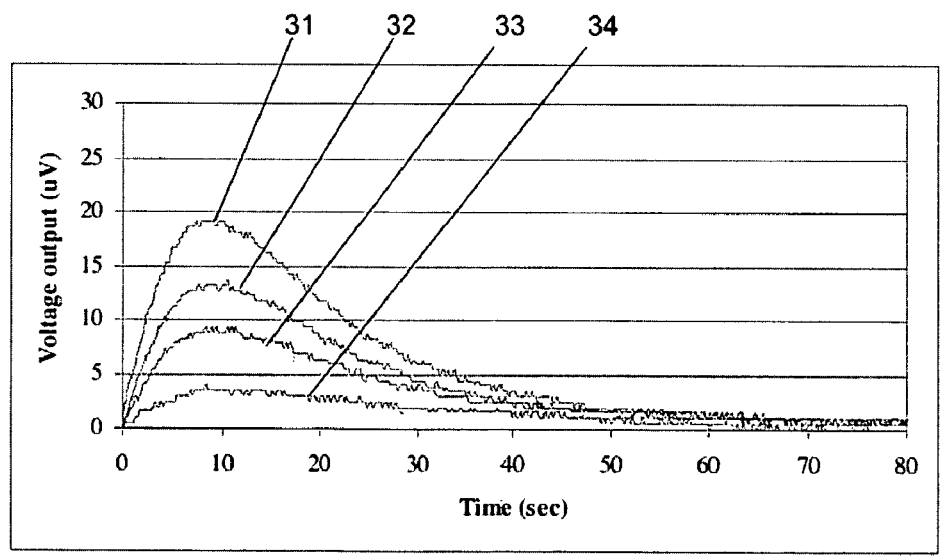
FIG. 6 shows the results of a test of the sensor illustrated in FIGS. 4 and 5 for four analyte concentrations.

FIG. 6 shows the results of a test with acetone in air reacting with a trichloroisocyanuric acid reactant. Curves 31, 32, 33, and 34 show the output voltage (in microvolts) as a function of time (in seconds) for an acetone concentration of 455, 325, 145, and 65 ppm respectively.

Figure 7:
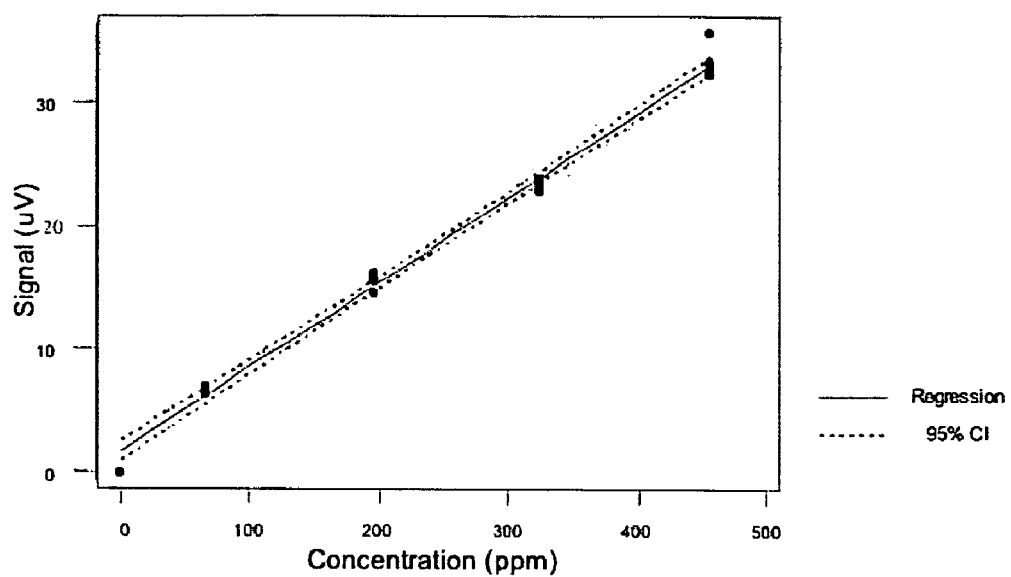
FIG. 7 summarizes sample test results by showing the peak sensor output voltage as a function of analyte concentration.

FIG. 7 shows the result of the same apparatus as a function of acetone concentration in ppm. Pulses of acetone of various concentrations were admitted to the conduit and the signal measured. The aspect of the raw data shown as the signal in FIG. 7 is the peak voltage output measured by the sensor. As may be seen, there is a very strong correlation between signal voltage and concentration. Thus, making a calibrated system should be quite practical.

Figure 8:
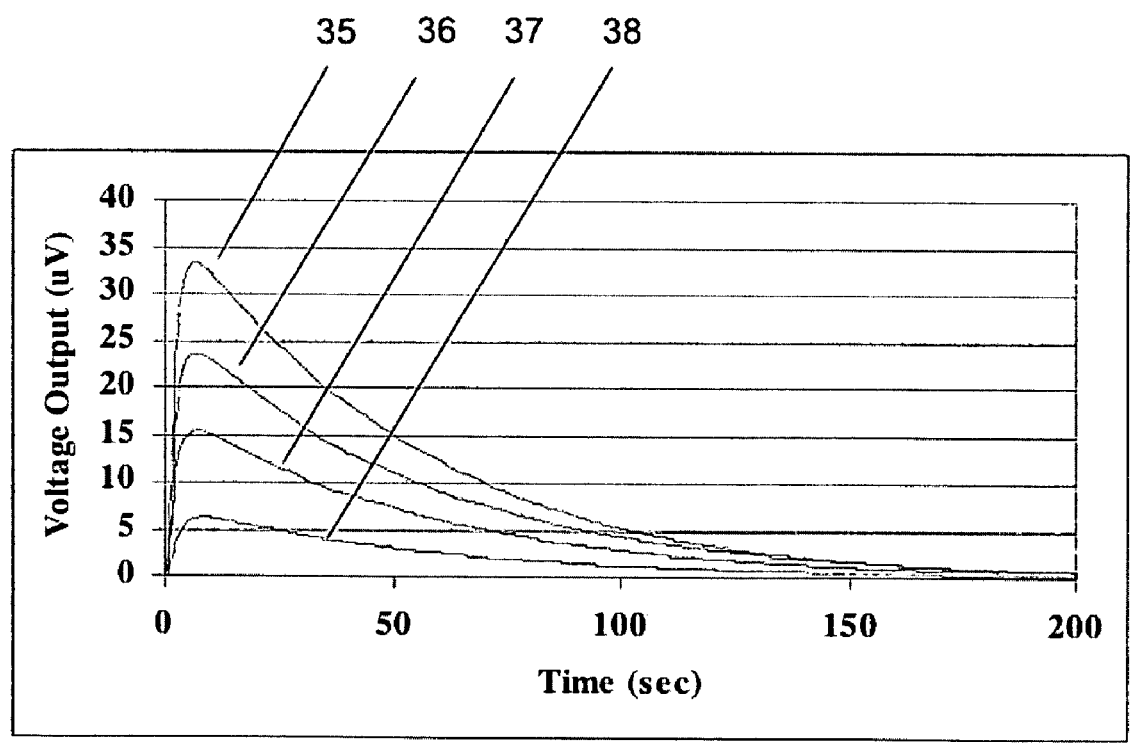
FIG. 8 shows theoretical curves for the same sensor and analyte concentrations as show in FIG. 6.

FIG. 8 shows theoretical curves generated by a mathematical model for the same sensor and analyte concentrations as show in FIG. 6. Similarly, curves 35, 36, 37, and 38 show the output voltage (in microvolts) as function of time for an acetone concentration of 455, 325, 145, and 65 ppm respectively.

Example 3

This example discusses the sensor setup for the case when the analyte is brought into contact with the thermopile sensor principally via diffusion. In other words, the thermopile sensing unit would operate in a stagnant or low flow environment.

A large glass Petri dish was used to simulate this system. The thermopile was mounted as described in Example 2. This unit was adhered centrally to the base of the Petri dish. The electrical leads from the thermopile were vertically suspended. The top of the Petri dish was covered rigorously with two pieces of Parafilm®, allowing the leads to exit the dish. (Parafilm® is a flexible film commonly used for sealing or protecting items such as flasks, trays, etc. and is a product of the American Can Company.) This setup was immobilized.

Instead of introducing acetone by creating flow over the thermopile, liquid acetone was injected into the Petri dish. Thus, acetone was allowed to evaporate into the ambient above the dish. Once acetone molecules were in the vapor phase, they diffuse to the surface of the thermopile and begin to interact. This setup was tested with hypochlorous acid, sodium hypochlorite, trichloroisocyanuric acid, and sodium dichloroisocyanurate dihydrate.

Figure 9:
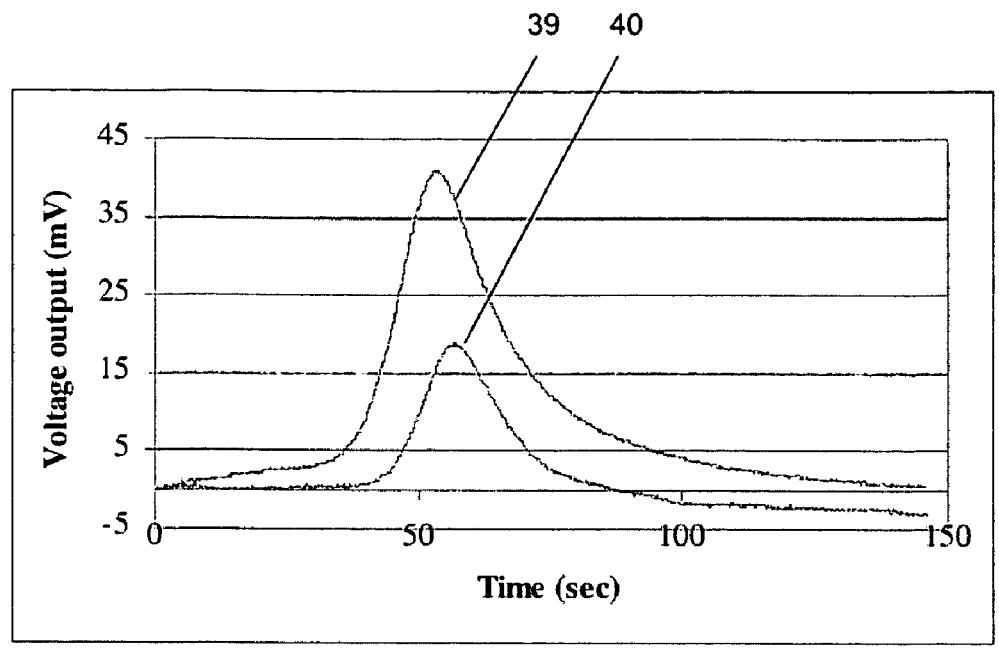
FIG. 9 shows the sensor response to analyte that was transferred only by diffusion.

FIG. 9 shows the experimental results generated by this embodiment. As shown, curve 40 has half the acetone concentration as curve 39. The acetone concentrations may be high for physiological applications. However, the significance is that the sensor is capable of measuring analytes that are transferred to the sensor by diffusion only. While it may appear that the process is slow due to the peak at 50 seconds, it is important to note that the analyte, in this case acetone, was injected in liquid form and had to evaporate and then diffuse to the surface of the device prior to any possible reaction.

Example 4

Figure 10:
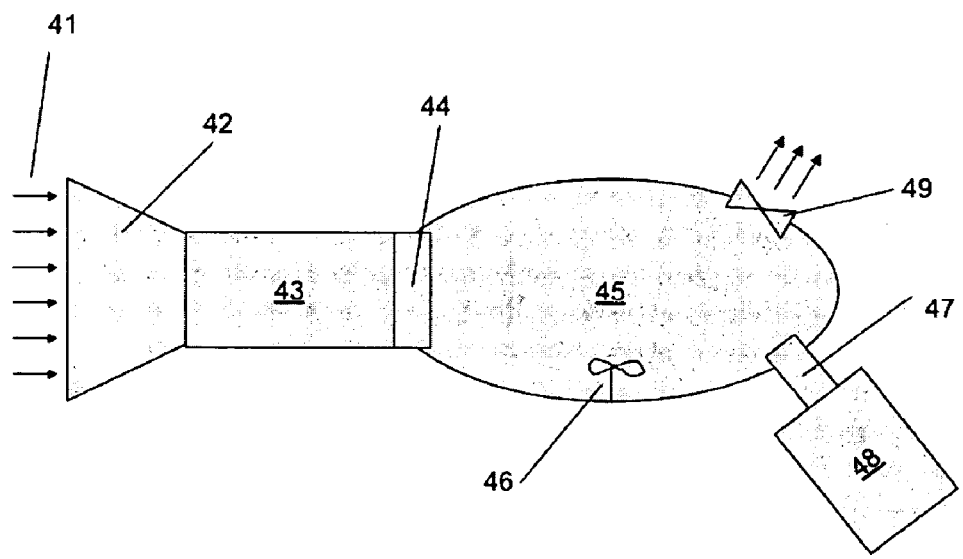
FIG. 10 shows a possible embodiment for use in a hospital environment using a patient gas mask.

FIG. 10 shows a possible embodiment for use in a hospital environment using a patient gas mask. Expired air 41 is generated either from the oral or nasal cavities. The breath is captured by a face mask 42 (which may be of standard gas mask design or some other) and is then directed through a polyethylene tube 43 where it is then filtered by a particle filter 44. The breath is directed by the tubing to a distendable volume 45 that is well-stirred by fan or other method 46. The flow of the breath through a channel 47 that leads to a chamber 48 containing the sensor can be controlled by a valve 49 that leads to the ambient environment.

The distendable volume 45 would allow for well-mixed fluid to enter the channel 47 in a regulated, laminar flow manner. As a result, variations in patient breath such as flow velocity patterns, interfering substances, temperature gradients, and particulate matter would be controlled, normalized, and mixed prior to introduction to the sensor inside chamber 48. This is useful, for instance, because the first volume of expired air is non-physiologically active (i.e. lung dead space).

The filter 44 is used because it may also be desirable to filter the breath before it enters volume 45. Different types of filters may be employed. First, a particle filter can be used. There are, of course, varying levels of particle size, shape, and type that can be considered. A simple particle filter, primarily to remove food residue, should suffice. Second, there are many filters which remove moisture from the breath. For instance, the entering breath can be directed to a channel wherein a water absorbent such as silica gel is immobilized and which will absorb all of the water. As may be appreciated, this may or may not be desirable depending on whether water is needed for the chemical reaction.

In this environment, the sensor could be used for continuous monitoring of patients. Suitable, well known, electronics could be used to communicate with nurses' stations, hospital computers or set of local alarms.

A very important analyte is ammonia. Breath ammonia is found in elevated concentration in patients with renal or liver failure. If ammonia were the analyte in the gas, ammonia can react with many different substances. As an example, ammonia reacts with hydrochloric acid to form ammonium chloride. The ammonium chloride will subsequently react with barium hydroxide to form barium chloride, ammonia, and water. This will allow for a two-step reaction sequence thereby increasing the total enthalpy of the reaction producing an amplification of the enthalpy.

It is important to note that this device can be used to measure the concentration of multiple analytes simultaneously. Thus, by use of multiple thermopiles, an entire screening can be performed with one breath.

Figure 11:
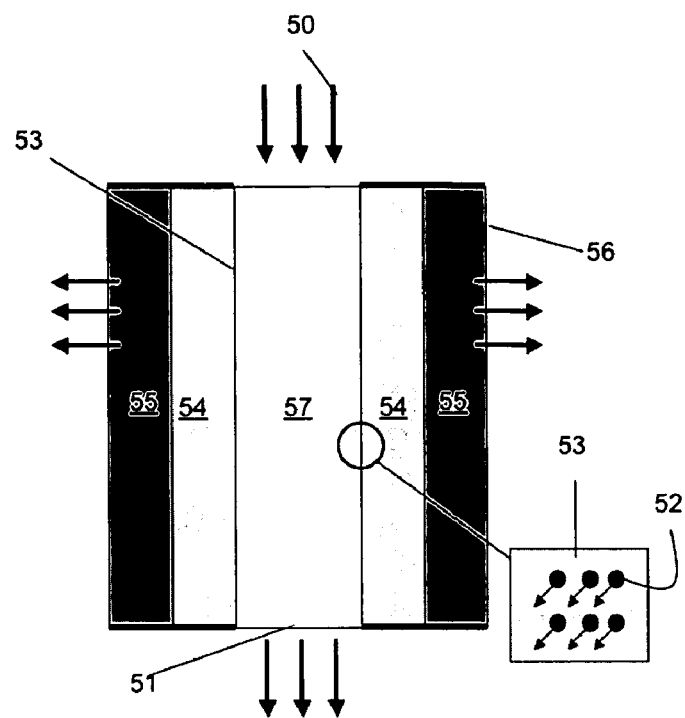
FIG. 11 shows a first possible chemical immobilization technique for chemical amplification.
Figure 13:
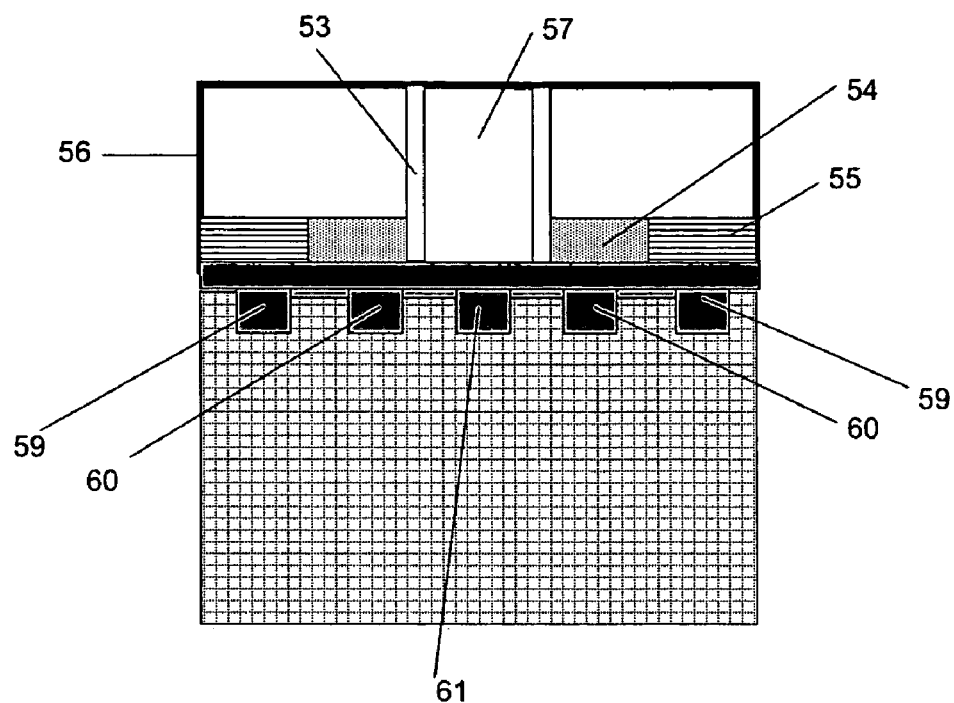
FIG. 13 depicts a side view of the technique shown in FIG. 11 and FIG. 12.

FIG. 11 shows a first possible chemical immobilization technique for chemical amplification. The gas containing the analyte 50 enters the conduit 57. Some of the gas exits at the end of the conduit. However, some of the gas passes through the pores 52 of the channel wall 53. Next to the channel wall, one interactant 54 is located and then a second interactant 55. This gas leaves the conduit through the outer semi-permeable conduit walls 56. Referring to FIG. 13, the thermopile consists of reference junctions 61 and sensing junctions 59 and 60. The sensing junctions can be single or multiple sets, depending upon the physical size of the junctions.

Figure 12:
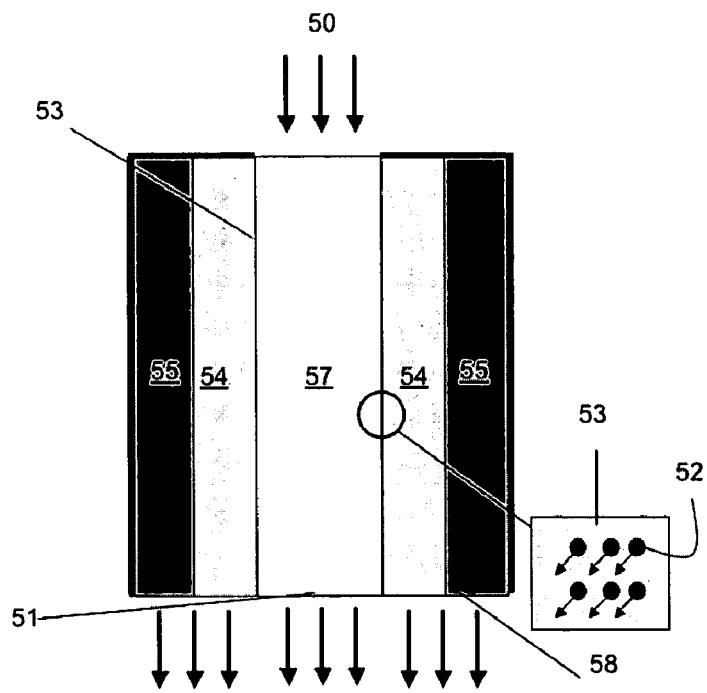
FIG. 12 shows a second possible chemical immobilization technique for chemical amplification.

FIG. 12 shows a second possible method of immobilizing the chemical. In this case, the wall 56 is impermeable and all gases flow through the conduits.

Example 5

Figure 14:
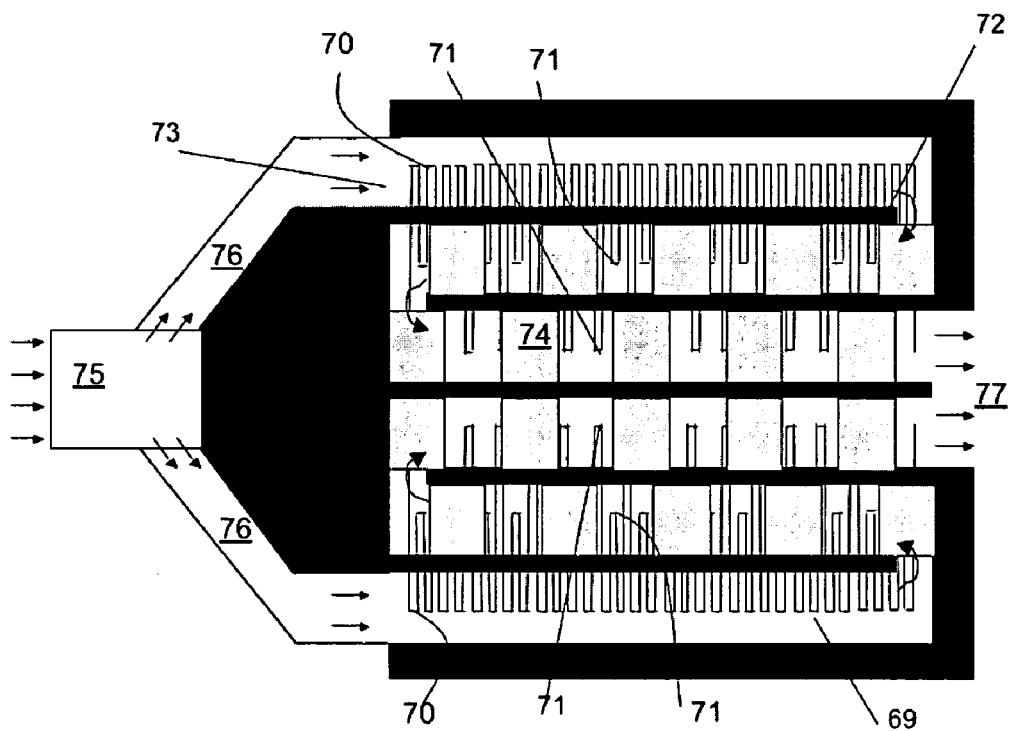
FIG. 14 shows the top view of a possible embodiment of an optimized chemical sensor.
Figure 15:
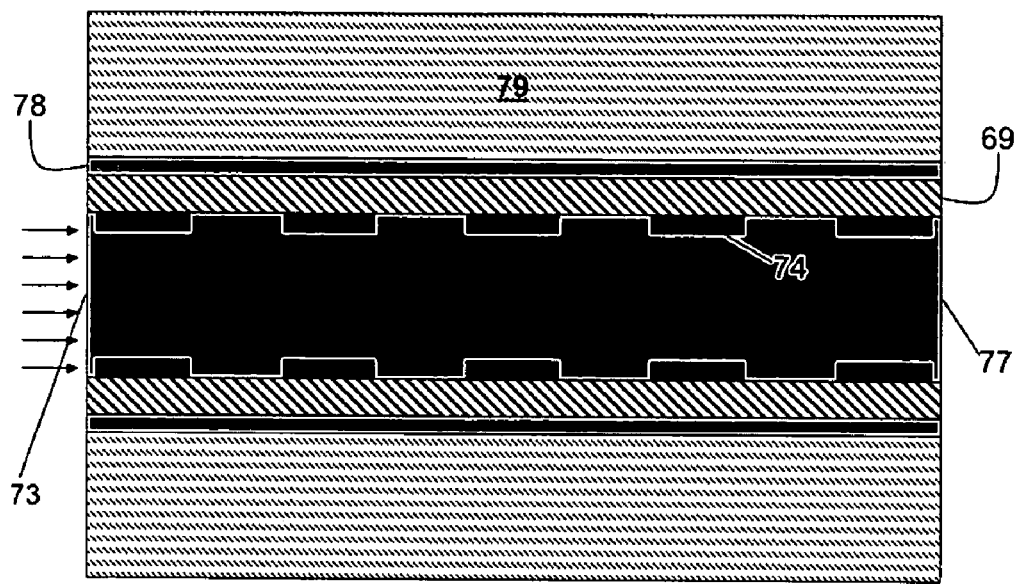
FIG. 15 depicts the side view of a possible embodiment of an optimized chemical sensor.

Reference will now be made to FIGS. 14 and 15. In operation, the fluid 75 enters the conduit through a mouthpiece. The fluid flow 75 is then divided between two tubes 76 both of which direct the fluid 75 into the reaction chamber, which is insulated. The fluid 75 first passes across a set of reference junctions 70. Then, the fluid 75 changes direction and begins to pass over the first set of sensing junctions 71 of the thermopile. The sensing junctions 71 are each coated with interactant 74. However, the sensing junctions 71 are separated from one another by the legs of the thermocouple, with further sensing junctions 71 in a subsequent channel. Therefore, the fluid 75 passes over a section of interactant 74 and then a section where interactant 74 is absent. Once again, the fluid 75 changes direction and passes over a second set of sensing junctions 71, which are distributed in the same way as described earlier. Finally, the fluid 75 exits the chamber at the opening 77 at the back-end.

FIG. 15 shows a cross section having the structure of FIG. 13. Interactant 74 is deposited on thin film substrate 69 on which is deposited sensor thermopile material 78. The device is surrounded by a thermal insulating structure 79. Fluid flow 73 carries the analyte past the interactants 74. As analyte is taken up by the interactant, its concentration drops in the layers next to the top and bottom. Diffusion from the center acts to replenish the depletion, but it is believed that this will usually not be enough to compensate. After passing the interactants 74, the concentration next to the top an bottom is not depleted, but is replenished by diffusion from the mid part of the flow. Based on theoretical considerations, the rate of uptake at a subsequent downstream interactant will be higher than if there were no replenishment zone. Thus, the uptake process is more efficient. Less total interactant in the device can be used for the same overall uptake of analyte.

This use of a replenish zone between interactant zones has quite general utility. Dilute solutions of almost all analytes in almost all fluids and gases will diffuse based on a concentration gradient. If the reaction with the interactants produces heat, then a heat sensor such as a thermopile is the best choice. However, any reaction that produces a reaction that can be sensed would benefit from this design. The only requirement is that it is possible to make a plurality of sensors and distribute them along the conduit. Even this may not be always necessary. For example, if the reaction produces electromagnetic radiation (such as light or infrared radiation) a remote sensor, such as a camera, could view the reaction at all interactants simultaneously.

The dimensions for this embodiment are provided. The mouthpiece should have dimensions of approximately 0.0212 m, the reaction chamber will be a conduit with a square-shaped cross-section of dimensions 0.0762×0.0762 $m^2$. Each channel is 0.0106 m wide and the channel barriers are 0.00254 m each. There are six channels and five channel barriers. The chemical is immobilized for lengths of 0.001 m with gaps between chemical of 0.001 m distance. The chemical is immobilized with appropriate particle size to engage in a reaction with a thickness of about 0.001 m. The channel height is 0.0206 m. The thickness of the thermopile metals can vary, but as in the previous examples, the metals are approximately 3 μm thick and the Kapton substrate is approximately 50 μm.

Compared with the chemistry and analyte of the working prototype tested in Example 1, this device is expected to increase the signal generated by a factor of approximately 100 times at least.

As illustrated, the replenishment zone relies on diffusion only. However, the replenishment of the outer layers could be augmented by providing mixing. This happens to some extent as the fluid makes a turn in the serpentine path in FIG. 13. However, obstructions could be placed in the center of the conduit after each interaction zone. They could be round wires stretched across the center of the conduit. Small flat plates may create more turbulence and better mixing.

In addition to passive measure, one could use mechanical agitation. This could be provided with piezoelectric elements or by shaking the entire device.

One cannot increase the concentration in the outer layers more than the average in the flow. However, one can bring it up from the depleted level after each interaction region. Of course, there are diminishing returns. However, normally one would not try to take up all of the analyte; just enough to get a strong signal. Theoretical, if the interaction regions are made vanishingly small and large in number, this device uses the least amount or interactant for any given signal.

Example 6

Chemical reactions in the liquid phase are generally better studied than those in the vapor phase. In aqueous solutions, hydrogen and hydroxide ions are often involved in acid or base-catalyzed reactions. One possible embodiment of the invention shown in FIG. 16 provides a method by which the analyte in the gas may be condensed to liquid form.

Figure 16:
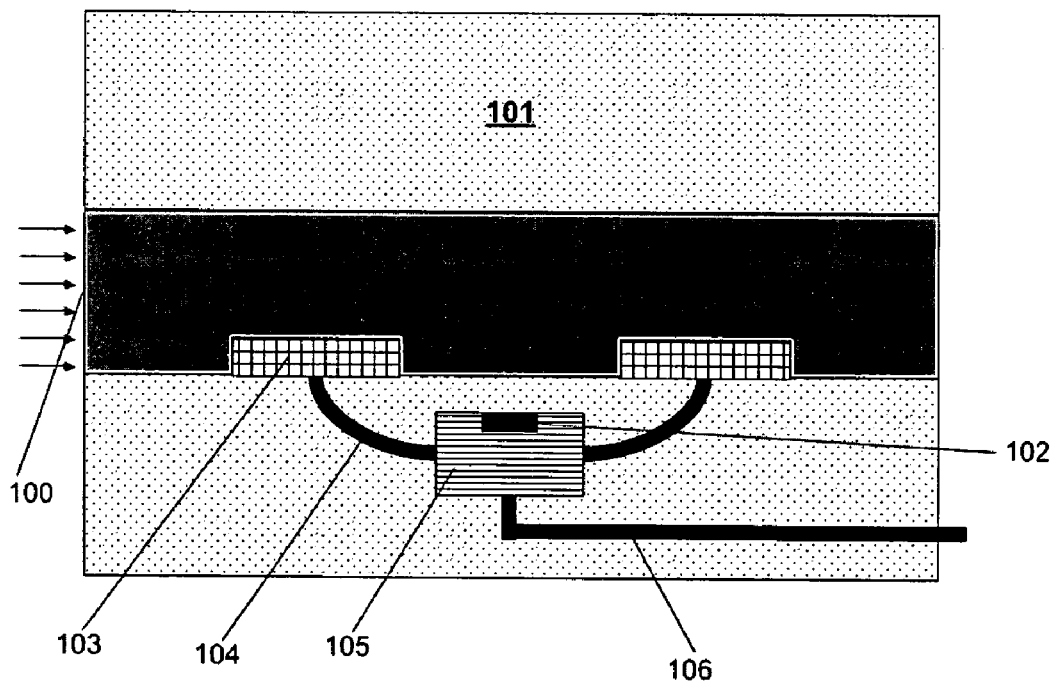
FIG. 16 shows a possible embodiment of a gas sensor using a condenser.

The sensor shown in FIG. 16 is designed to condense a gas to a liquid. In medical applications, the breath would condense prior to exposure to the sensor. This embodiment takes advantage of the improved diffusivity of analytes in a gas as compared to in a liquid. Simultaneously, the heat loss in a liquid is far less than in a gas under similar physical conditions. This design also allows one to take advantage of the well-researched liquid-phase acetone reactions.

As may be appreciated, one of the problems that frequently arises with chemical sensors is chemical depletion. In other words, the chemical reactant is consumed over a period of time. One way to circumvent this problem is to use chemistries that have a long lifetime and/or are not consumed in the reaction (enzymes or catalysts). However, even if an enzyme is used instead of an inorganic chemical, enzyme deactivation or degradation remains a problem. Here two embodiments of the present invention are presented which specifically address the aforementioned problem.

Figure 17:
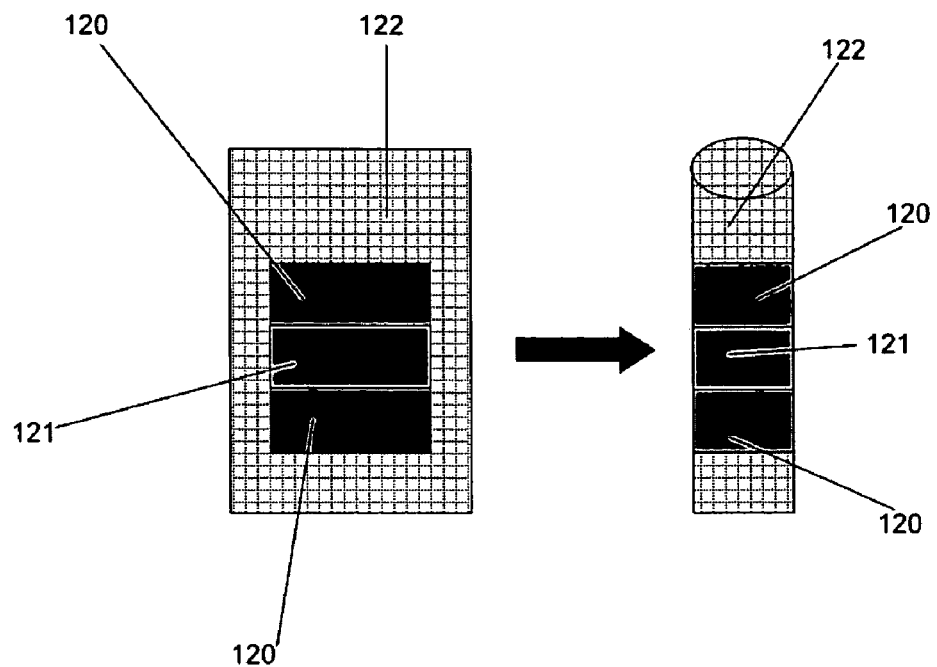
FIG. 17 depicts a possible method for creating a thermopile in a catheter style.

In one embodiment, the sensor is made "removable" from the overall breath collection chamber. This is done by fashioning the sensor as a probe or by fashioning the substrate such that it takes on a three-dimensional shape, for instance, of a catheter. FIG. 17 shows the thermopile where the sensing junctions are positioned in one area 120 and the reference junctions in another area 121. The substrate 122 is folded to form a cylindrical tube. If the substrate on which the thermopile is deposited is flexible, then the thermopile itself can be formed around, for example, a cylindrical insulator. In this way, the thermopile can be made into a catheter-style device.

Figure 18:
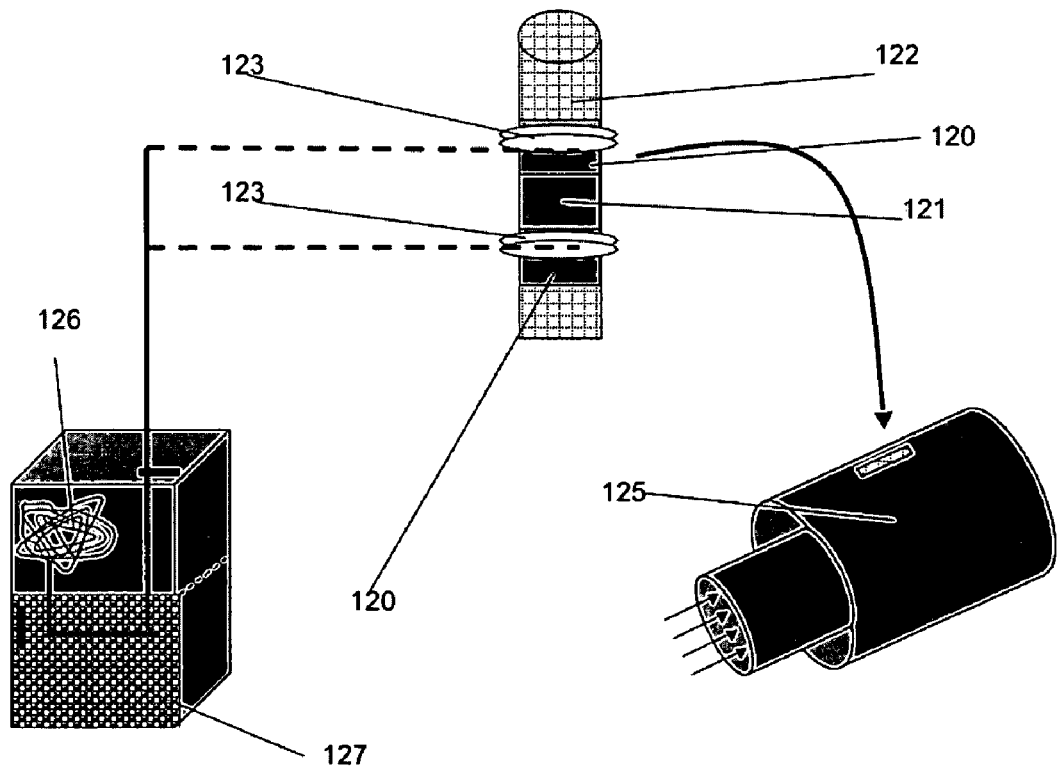
FIG. 18 shows a possible method for immobilizing chemical on the sensor described by FIG. 17.
Figure 19:
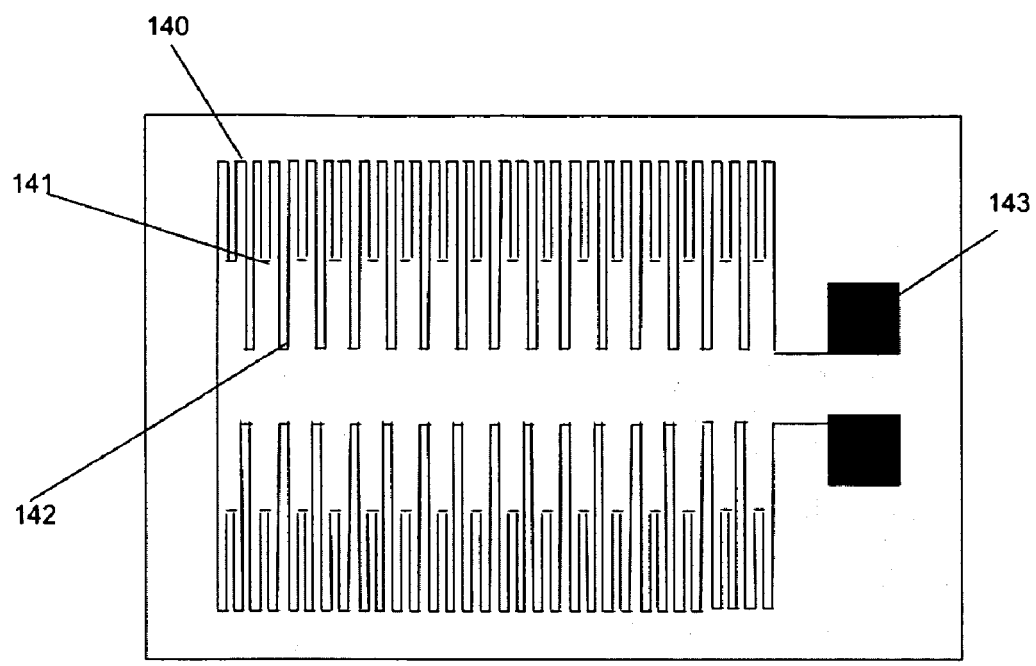
FIG. 19 shows a possible embodiment of a thermopile.
Figure 20:
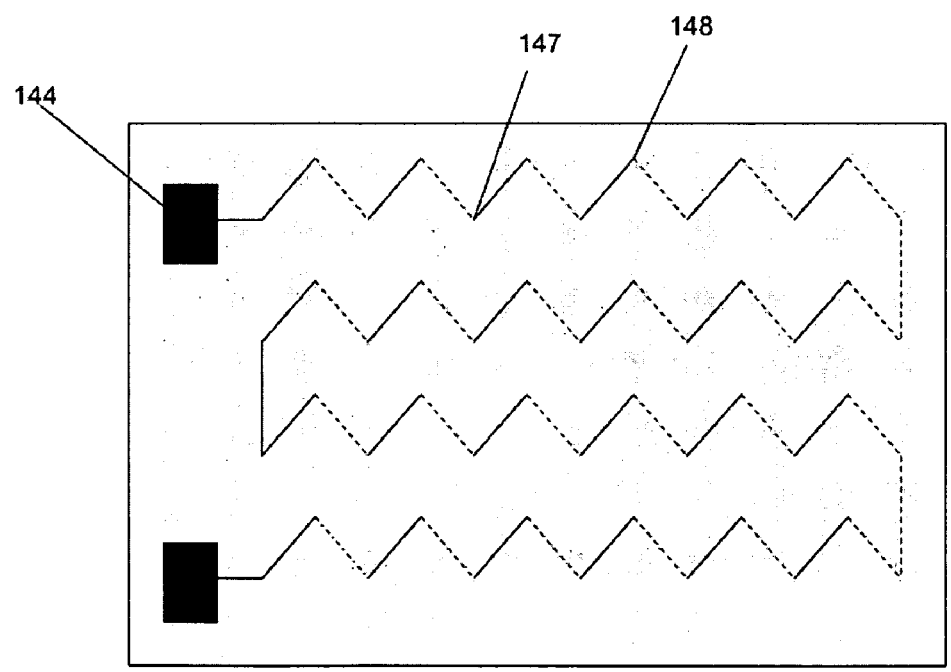
FIG. 20 shows a possible embodiment of a thermopile.

In another embodiment, a thin absorbent material exposed to some interactant, for example hypochlorous acid, is wrapped around the sensing junctions of the thermopile. Optionally, the reference junctions may be wrapped with a non-exposed absorbent material. FIG. 18 shows a possible method by which chemical can be immobilized on the thermopile in, for example, the embodiment described in FIG. 17. A material 126 is exposed to a chemical interactant 127 and the interactant-coated threading material 123 is wrapped around the sensing junctions 120 and the reference junctions are either coated with unexposed material 126 or left uncoated. In a possible embodiment, the entire thermopile with material is placed in a chamber 125 wherein the analyte interacts with it.

While the subject invention has been illustrated and described in detail in the drawings and foregoing description, the disclosed embodiments are illustrative and not restrictive in character. All changes and modifications that come within the scope of the invention are desired to be protected.

What is claimed is:

1. An apparatus for detecting an analyte in a fluid, the apparatus comprising:
    first and second analyte reaction surfaces disposed in series with respect to one another, and a conduit for channeling said analyte-containing fluid past the first and second analyte reaction surfaces in series, an interactant being disposed on said first and second analyte reaction surfaces that reacts with the analyte to produce an interaction that can be sensed, the interactant on the first and second analyte reaction surfaces being the same;
    a sensor disposed to detect said interaction for the first and second analyte reaction surfaces; and
    at least one replenishment region disposed between said first and second analyte reaction surfaces, whereby analyte concentration in said fluid that was depleted by said interaction at the first analyte reaction surface is replenished before contacting the second analyte reaction surface.

2. The apparatus of claim 1, wherein said fluid is in a gas phase and said conduit channels the gas phase fluid past the first and second analyte reaction surfaces in series.

3. The apparatus of claim 1, wherein said fluid comprises air and said conduit channels the air past the first and second analyte reaction surfaces in series.

4. The apparatus of claim 1, wherein said sensor is selected from a group of sensors consisting of thermistors, thermocouples, thermopiles, ion sensors, and radiation sensors.

5. The apparatus of claim 1, further comprising at least one temperature compensating reference sensor.

6. The apparatus of claim 1, wherein the interactant disposed on the reaction surfaces physically reacts with the analyte to produce a physical interaction, the sensor is disposed to detect the physical interaction, and the at least one replenishment region replenishes the analyte concentration in the fluid that was depleted by the physical interaction.

7. The apparatus of claim 1, wherein the interactant disposed on the reaction surfaces chemically reacts with the analyte to produce a chemical interaction, the sensor is disposed to detect the chemical interaction, and the at least one replenishment region replenishes the analyte concentration in the fluid that was depleted by the chemical interaction.

8. An apparatus as recited in claim 1, wherein the replenishment region is equal to the length of the first analyte reaction region.

9. An apparatus as recited in claim 1, wherein the replenishment region is greater than the length of the first analyte reaction region.

10. An apparatus for detecting an analyte in a fluid, the apparatus comprising:
first and second analyte reaction surfaces disposed in series with respect to one another, and a conduit for channeling said analyte-containing fluid past the first and second analyte reaction surfaces in series, an interactant being disposed on said first and second analyte reaction surfaces that reacts with the analyte to produce an interaction that can be sensed, the interactant on the first and second analyte reaction surfaces being the same;
a sensor disposed to detect said interaction for the first and second analyte reaction surfaces; and
at least one replenishment region disposed between said first and second analyte reaction surfaces, whereby analyte concentration in said fluid that was depleted by said interaction at the first analyte reaction surface is replenished before contacting the second analyte reaction surface,
wherein said interactant is selected from a group of hydrogenation reactants consisting of Raney nickel and platinum.

11. An apparatus for detecting an analyte in a fluid, the apparatus comprising:
first and second analyte reaction surfaces disposed in series with respect to one another, and a conduit for channeling said analyte-containing fluid past the first and second analyte reaction surfaces in series, an interactant being disposed on said first and second analyte reaction surfaces that reacts with the analyte to produce an interaction that can be sensed, the interactant on the first and second analyte reaction surfaces being the same;
a sensor disposed to detect said interaction for the first and second analyte reaction surfaces; and
at least one replenishment region disposed between said first and second analyte reaction surfaces, whereby analyte concentration in said fluid that was depleted by said interaction at the first analyte reaction surface is replenished before contacting the second analyte reaction surface,
wherein said interactant is selected from a group of adsorbents consisting of activated charcoal and activated carbon impregnated with halogen compounds.

12. An apparatus for detecting an analyte in a fluid, the apparatus comprising:
first and second analyte reaction surfaces disposed in series with respect to one another, and a conduit for channeling said analyte-containing fluid past the first and second analyte reaction surfaces in series, an interactant being disposed on said first and second analyte reaction surfaces that reacts with the analyte to produce an interaction that can be sensed, the interactant on the first and second analyte reaction surfaces being the same;
a sensor disposed to detect said interaction for the first and second analyte reaction surfaces; and
at least one replenishment region disposed between said first and second analyte reaction surfaces, whereby analyte concentration in said fluid that was depleted by said interaction at the first analyte reaction surface is replenished before contacting the second analyte reaction surface,
wherein said replenishment region comprises a portion of conduit having walls disposed between said reaction surfaces that are non-reactive with the analyte.

13. The apparatus of claim 12, wherein said replenishment region further comprises an obstruction disposed therein.

14. An apparatus for detecting an analyte in a fluid, the apparatus comprising:
first and second analyte reaction surfaces disposed in series with respect to one another, and a conduit for channeling said analyte-containing fluid past the first and second analyte reaction surfaces in series, an interactant being disposed on said first and second analyte reaction surfaces that reacts with the analyte to produce an interaction that can be sensed, the interactant on the first and second analyte reaction surfaces being the same;
a sensor disposed to detect said interaction for the first and second analyte reaction surfaces;
at least one replenishment region disposed between said first and second analyte reaction surfaces, whereby analyte concentration in said fluid that was depleted by said interaction at the first analyte reaction surface is replenished before contacting the second analyte reaction surface; and
at least one temperature compensating reference sensor,
wherein said sensor comprises top and bottom sensors, and said conduit comprises a spacing between the top and bottom sensors that is selected to be about two times the maximum thickness of the concentration boundary layer at the end of each reaction surface.

15. An apparatus for detecting an analyte in a fluid, the apparatus comprising:
a plurality of analyte reaction surfaces disposed in series with respect to one another, and a conduit for channeling said analyte-containing fluid nonlinearly past the plurality of analyte reaction surfaces, an interactant being disposed on said reaction surfaces that reacts with the analyte to produce an interaction that can be sensed;
a sensor disposed to detect said interaction for the plurality of analyte reaction surfaces; and
at least one replenishment region disposed between selected ones of the plurality of analyte reaction surfaces, whereby analyte concentration in said fluid that was depleted by said interaction at the first analyte reaction surface is replenished before contacting the second analyte reaction surface.

16. The apparatus of claim 15, wherein said fluid comprises a gas phase and said conduit channels the gas phase fluid past the first and second analyte reaction surfaces in series.

17. An apparatus as recited in claim 15, wherein the conduit is non-linear.

18. An apparatus as recited in claim 15, wherein the conduit comprises a serpentine conduit having linear portions and curved portions, and the at least one replenishment region comprises the curved portions of the conduit.

19. An apparatus for detecting an analyte in a fluid, the apparatus comprising:
a plurality of analyte reaction surfaces disposed in series with respect to one another, and a conduit for channeling said analyte-containing fluid nonlinearly past the plurality of analyte reaction surfaces, an interactant being disposed on said reaction surfaces that reacts with the analyte to produce an interaction that can be sensed;
a sensor disposed to detect said interaction for the plurality of analyte reaction surfaces; and
at least one replenishment region disposed between selected ones of the plurality of analyte reaction surfaces, whereby analyte concentration in said fluid that was depleted by said interaction at the first analyte reaction surface is replenished before contacting the second analyte reaction surface, wherein the at least one replenishment region is disposed in the conduit.

20. An apparatus for detecting an analyte in a fluid, the apparatus comprising:
- a serpentine-shaped conduit comprising linear portions and at least one curved portion;
- a plurality of analyte reaction surfaces disposed in series in the conduit, at least one of the analyte reaction surfaces being disposed in at least two of the linear portions of the conduit, wherein flow of the fluid through the conduit causes the fluid to contact the plurality of analyte reaction surfaces; and
- an interactant being disposed on said analyte reaction surfaces that reacts with the analyte to produce an interaction that can be sensed.

21. An apparatus for detecting an analyte in a fluid, the apparatus comprising:
- first and second analyte reaction surfaces disposed in series with respect to one another, and a conduit for channeling said analyte-containing fluid past the first and second analyte reaction surfaces, an interactant being disposed on said reaction surfaces that reacts with the analyte to produce an interaction that can be sensed;
- a sensor disposed to detect said interaction for the first and second analyte reaction surfaces; and
- at least one replenishment region comprising a mixer that mixes the fluid received from the first analyte reaction surface and directs the mixed fluid to the second analyte reaction surface.

22. An apparatus as recited in claim 21, wherein the mixer comprises a piezoelectric mixing device.

23. An apparatus for detecting an analyte in a fluid, the apparatus comprising:
- first and second analyte reaction surfaces disposed in series with respect to one another, and a conduit for channeling said analyte-containing fluid past the first and second analyte reaction surfaces, an interactant being disposed on said reaction surfaces that reacts with the analyte to produce an interaction that can be sensed;
- a sensor disposed to detect said interaction for the first and second analyte reaction surfaces; and
- at least one replenishment region disposed between said first and second analyte reaction surfaces, the at least one replenishment region comprising an obstruction that changes flow of the fluid to cause the analyte concentration in said fluid at the second reaction surface to be replenished relative to the analyte concentration as the fluid departs the first analyte reaction surface.

24. An apparatus as recited in claim 23, wherein the obstruction comprises at least one wire.

25. An apparatus as recited in claim 23, wherein the obstruction comprises at least one plate.

26. An apparatus for detecting an analyte in a fluid, the apparatus comprising:
- first and second analyte reaction surfaces disposed in series with respect to one another, and a conduit for channeling said analyte-containing fluid past the first and second analyte reaction surfaces, an interactant being disposed on said reaction surfaces that reacts with the analyte to produce an interaction that can be sensed;
- a sensor disposed to detect said interaction for the first and second analyte reaction surfaces; and
- at least one replenishment region disposed between said first and second analyte reaction surfaces that changes the direction of flow of the fluid to the second analyte reaction surface relative to the first analyte reaction surface and replenishes the analyte concentration of the fluid at the second reaction surface relative to the analyte concentration of the fluid as the fluid departs the first analyte reaction surface.

27. An apparatus as recited in claim 26, wherein the at least one replenishment region comprises a nonlinear portion of the conduit.

28. An apparatus detecting an analyte in a fluid, the apparatus comprising:
- first and second analyte reaction surfaces disposed in series with respect to one another, and a conduit for channeling said analyte-containing fluid past the first and second analyte reaction surfaces, an interactant being disposed on said reaction surfaces that reacts with the analyte to produce an interaction that can be sensed;
- a sensor disposed to detect said interaction for the first and second analyte reaction surfaces; and
- at least one replenishment region disposed between said first and second analyte reaction surfaces that changes the direction of flow of the fluid to the second analyte reaction surface relative to the first analyte reaction surface and replenishes the analyte concentration of the fluid at the second reaction surface relative to the analyte concentration of the fluid as the fluid departs the first analyte reaction surface,
- wherein the at least one replenishment region comprises an obstruction.

29. An apparatus for detecting an analyte in a fluid, the apparatus comprising:
- first and second analyte reaction surfaces disposed in series with respect to one another, and a conduit for channeling said analyte-containing fluid past the first and second analyte reaction surfaces, an interactant being disposed on said reaction surfaces that reacts with the analyte to produce an interaction that can be sensed;
- a sensor disposed to detect said interaction for the first and second analyte reaction surfaces; and
- at least one replenishment region disposed between said first and second analyte reaction surfaces that changes the direction of flow of the fluid to the second analyte reaction surface relative to the first analyte reaction surface and replenishes the analyte concentration of the fluid at the second reaction surface relative to the analyte concentration of the fluid as the fluid departs the first analyte reaction surface,
- wherein the at least one replenishment region comprises a mixer.

* * * * *